United States Patent [19]
Kretsch et al.

[11] Patent Number: 5,233,520
[45] Date of Patent: Aug. 3, 1993

[54] METHOD AND SYSTEM FOR MEASUREMENT OF INTAKE OF FOODS, NUTRIENTS AND OTHER FOOD COMPONENTS IN THE DIET

[75] Inventors: Mary J. Kretsch, Vallejo; Moira A. Gunn; Alice K. Fong, both of San Francisco, all of Calif.

[73] Assignee: The United States of America as represented by the Secretary of Agriculture, Washington, D.C.

[21] Appl. No.: 631,011

[22] Filed: Dec. 19, 1990

[51] Int. Cl.$^5$ .............................................. G06F 15/00
[52] U.S. Cl. .......................... 364/413.29; 364/413.13
[58] Field of Search ....................... 364/413.29, 413.13

[56] References Cited

PUBLICATIONS

M. J. Kretsch et al., "Validation of a New Computerized Technique for Quantitating Individual Dietary Intake: The Nutrition Evaluation Scale . . . ", Amer. J. Clin. Nutr. 51: 477–484 (1990).
Fong et al., "Nutrition Evaluation Scale System Reduces Time and Labor in Recording Quantative Dietary Intake", J. Amer. Dietetic Assoc., 90(5): 664–670 (1990).
M. J. Kretsch "New Computerized Techniques for Assessing Food Intake", Chapter 10, Reprinted from Nutritional Status Assessment of the Indiv. by G. E. Livingston: 105–112 (Feb. 1989).
J. Amer. Dietetic Assn., 91(4): 00–00 (Apr. 1991), Advertisement for "Nutritionist III".
J. Amer. Dietetic Assn., 91(4): 00–00 (Apr. 1991), Advertisement for "The Food Processor II".
Sporting Edge Catalog, "New! World's Most Advanced Nutrition Scale Computes Detailed Analysis of 1,200 Foods" (date unavailable).
Nasco Nutrition Teaching Aids '89–'90 Catalog, Item #6, New Sunbeam ® "Nutriscale II" (date unavailable).
Fordham-Scope Catalog, "Polder Dietetic Computer" Model #8011 (Copyright 1988).
L. Stockley et al., "Description of a Food Recording Electronic Device for Use in Dietary Surveys," Human Nutr.:Appl. Nutr. 40A: 13–18 (1986).
"Computerized Food Scale System for Dietary Intake Assessment," Annual Research Progress Report for period Jan. 1986–Dec. 1986 (Jan. 1987).

(List continued on next page.)

Primary Examiner—Roy N. Envall, Jr.
Assistant Examiner—Gita D. Shingala
Attorney, Agent, or Firm—M. Howard Silverstein; John D. Fado; Margaret A. Connor

[57] ABSTRACT

An interactive computerized dietary measurement system and process which can be used by lay people for accurate measurement of the intake of foods, nutrients, and other food components in the diet. The system includes a computer device coupled with an electronic balance, output/display device(s), user input element(s), a food codes database and a storage element. The system has the ability to provide a plurality of weigh-in measurement options with respect to different food service settings or habits and to respectively tag the measurement of each of the options selected by the user in the storage element so as to track the measurements. The system can instruct user on the next measurement action and required input so that users are not required to remember all of the measurement actions and sequences of the actions for the measurements. The system also provides a plurality of weigh-out measurement options in which the computer will track the measurement record and remind the user of what has been done and what should be done so that a complete and accurate collection of dietary intake data can be achieved. The system is further capable of signalling to the user any weighing errors for allowing user to correct the errors, and of permitting user to make comments or notes as to measurements.

46 Claims, 23 Drawing Sheets

Presentation of Hardware Components

OTHER PUBLICATIONS

"Computerized Human Machine Interface for the Computerized Food Scale System" Annual Research Progress Report for period Sep. 1988–Dec. 1988 (Feb. 1989).

A. K. H. Fong et al., "The Ability of Research Volunteers to Accurately Identify Foods Using a Food Catalog Designed for the Computerized Food Scale System" Abstract in Proceedings of the Thirteenth National Nutrient Databank Conference, Framingham, Mass. (Jun. 6–8, 1988).

M. J. Kretsch et al., "Validation of a New Computerized Technique for Measuring Dietary Intake of Individuals," The FASEB Journal 2(4): A631 (1988) Abstract 1943.

M. J. Kretsch et al., "Comparison of the Computerized Food Scale System Versus the 24–Hour Recall to Measure Nutrient Intake of Individuals," Abstract, The American Dietetic Ass. 71st Annual Mtg., San Francisco, Calif. (Oct. 3–7, 1988).

M. J. Kretsch et al., "Accuracy of the Nutrition Evaluation Scale System (NESSy): Effect of Gender and Educational Level," Suppl. J. Amer. Dietetic Assn. 89(9): A–58 (1989).

M. J. Kretsch et al., "Nutrition Evaluation Scale System (NESSy): Effect of Recording Food Consumption with NESSy on Spontaneous Energy Intake of Men," Abstract, 2nd Mtg. on Nutritional Epidemiology, West Berlin, Germany (Oct. 23–25, 1989).

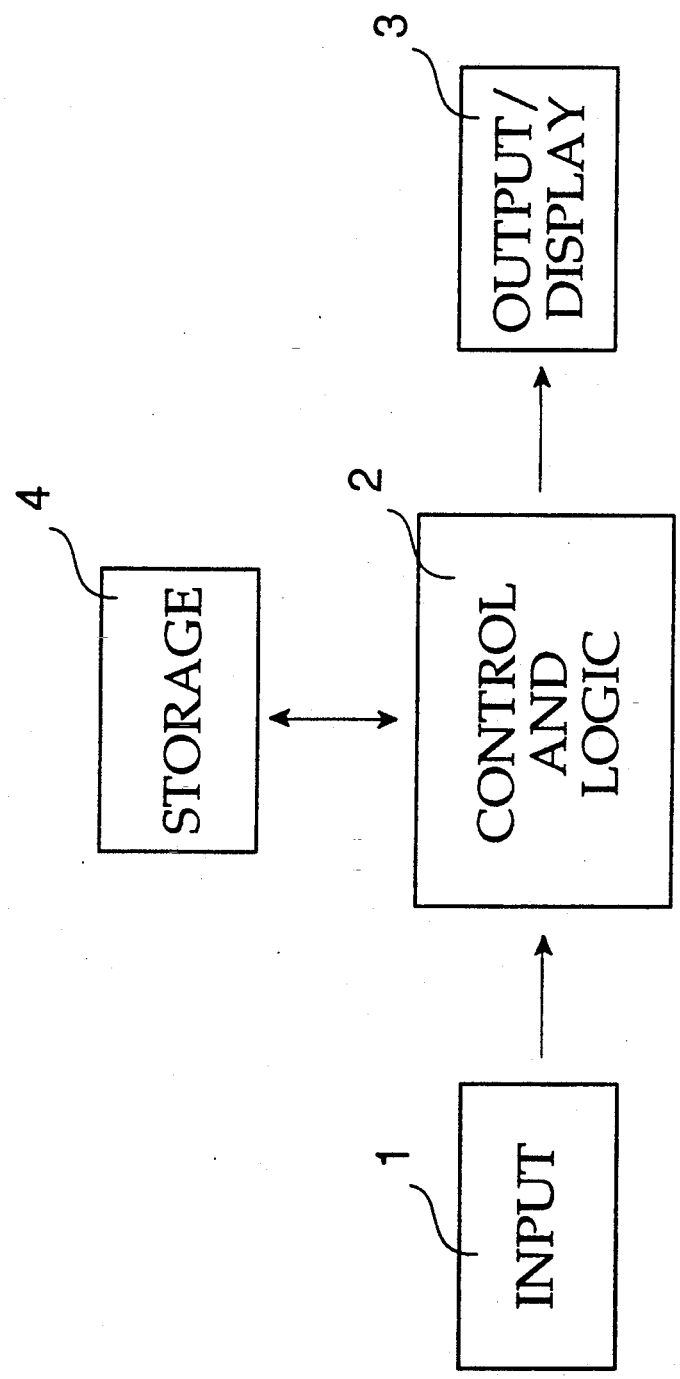
Fig. 1  Presentation of Primary Components

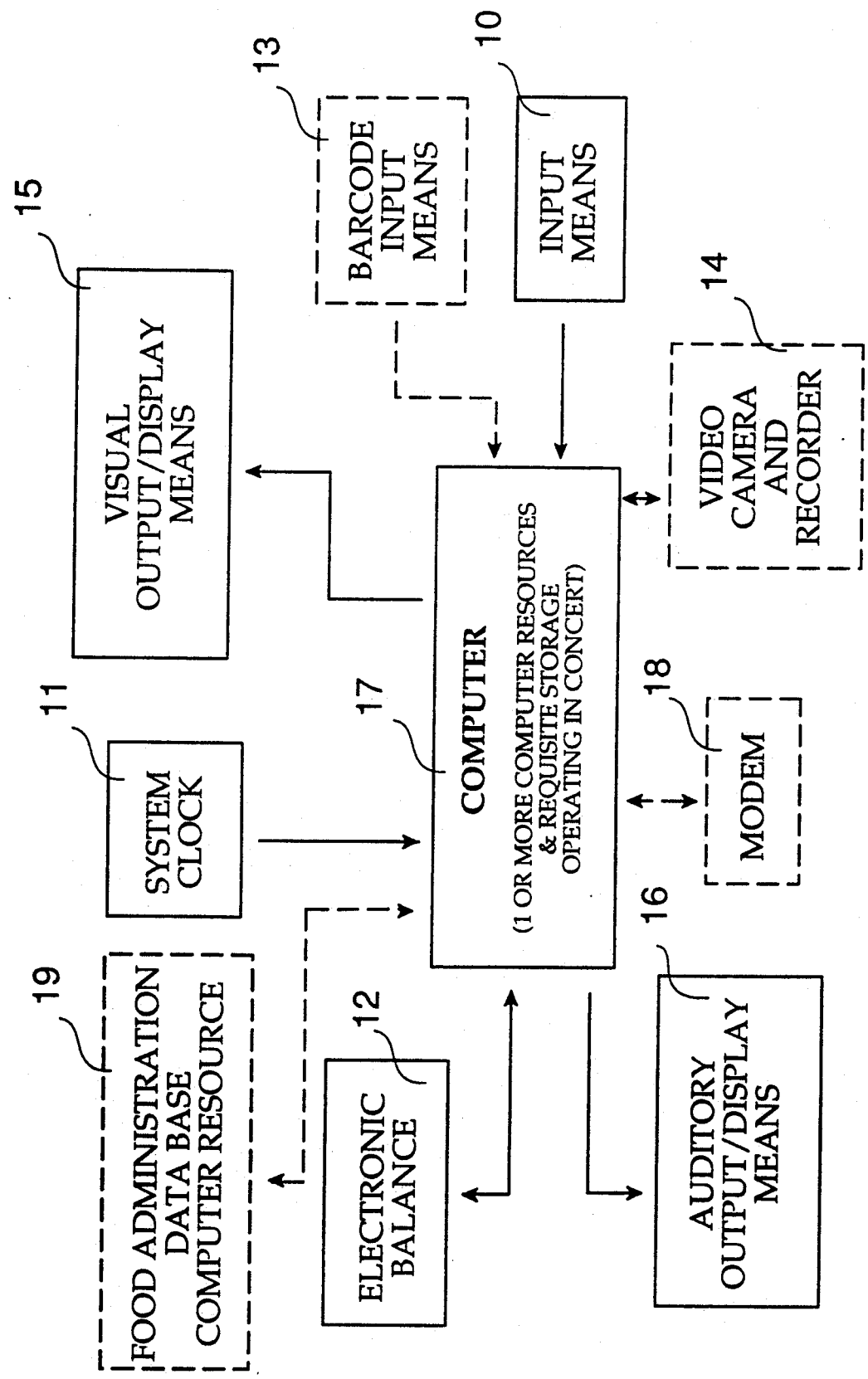
Fig. 2 Presentation of Hardware Components

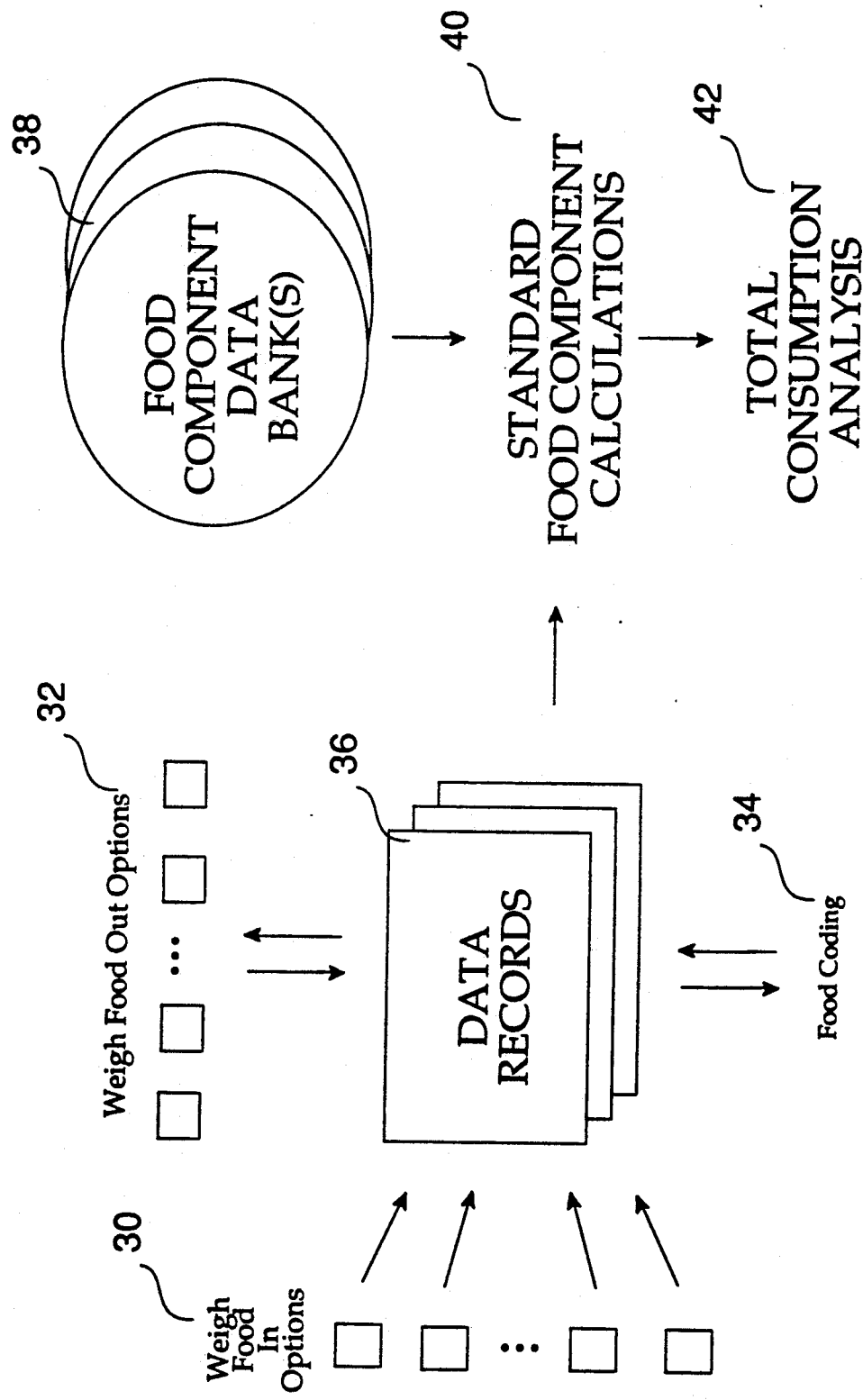
Fig. 3 Relation of Data Collection Methods to Consumption Analysis Process

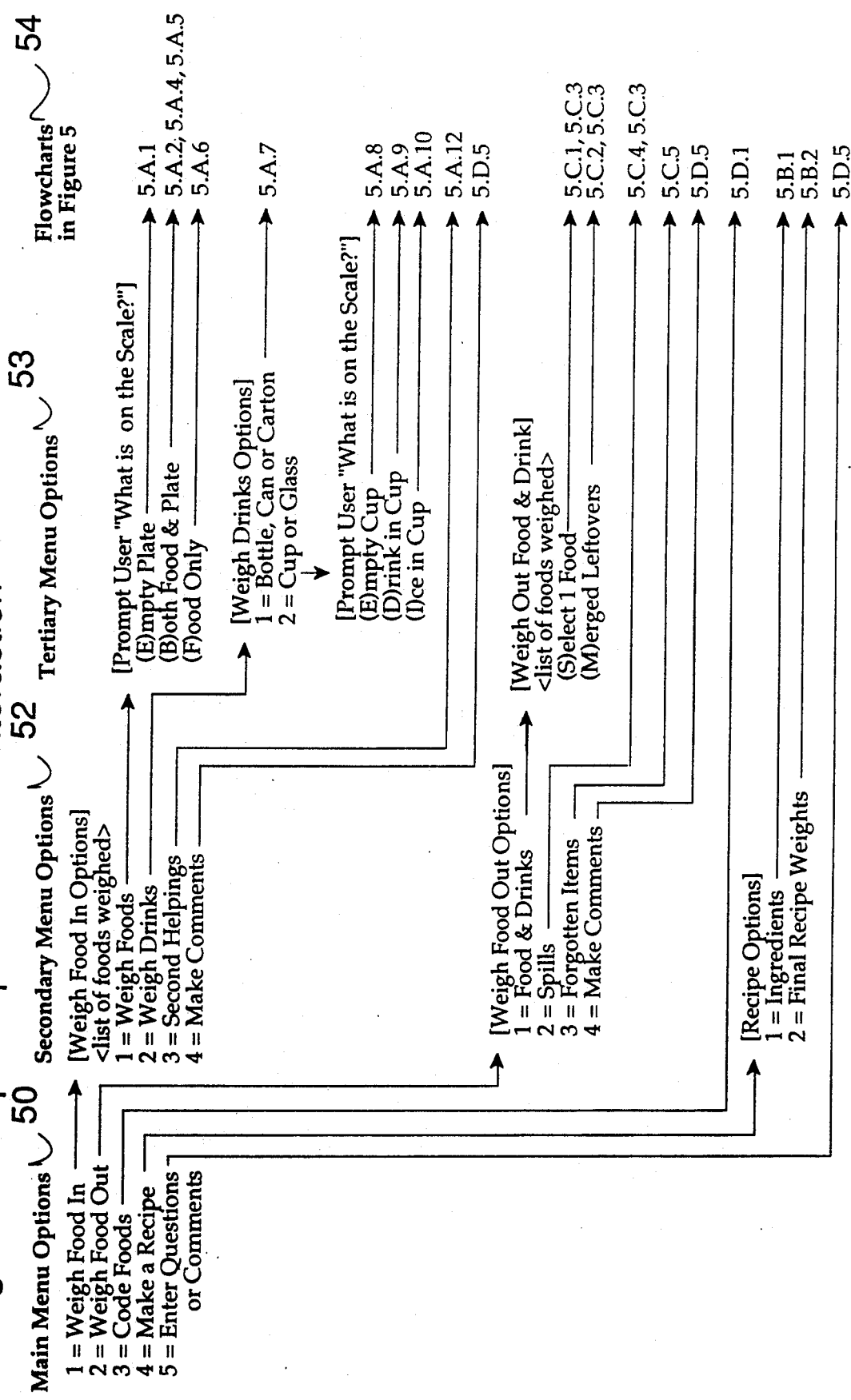
Fig. 4 Sample Top-Level User Interaction

Fig. 5 Data Collection Methods
5.A. Individual Intake Food Weigh-In Methods
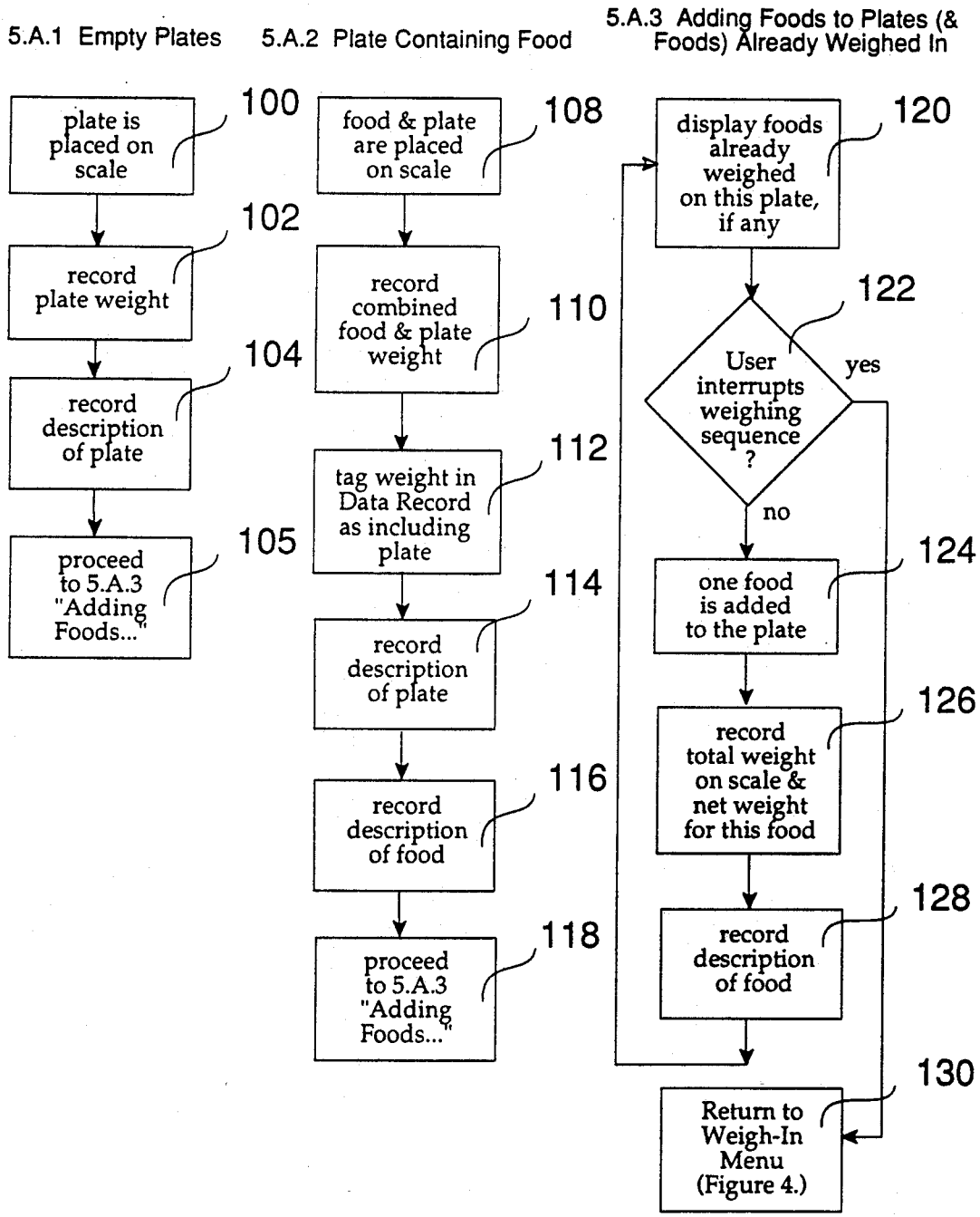

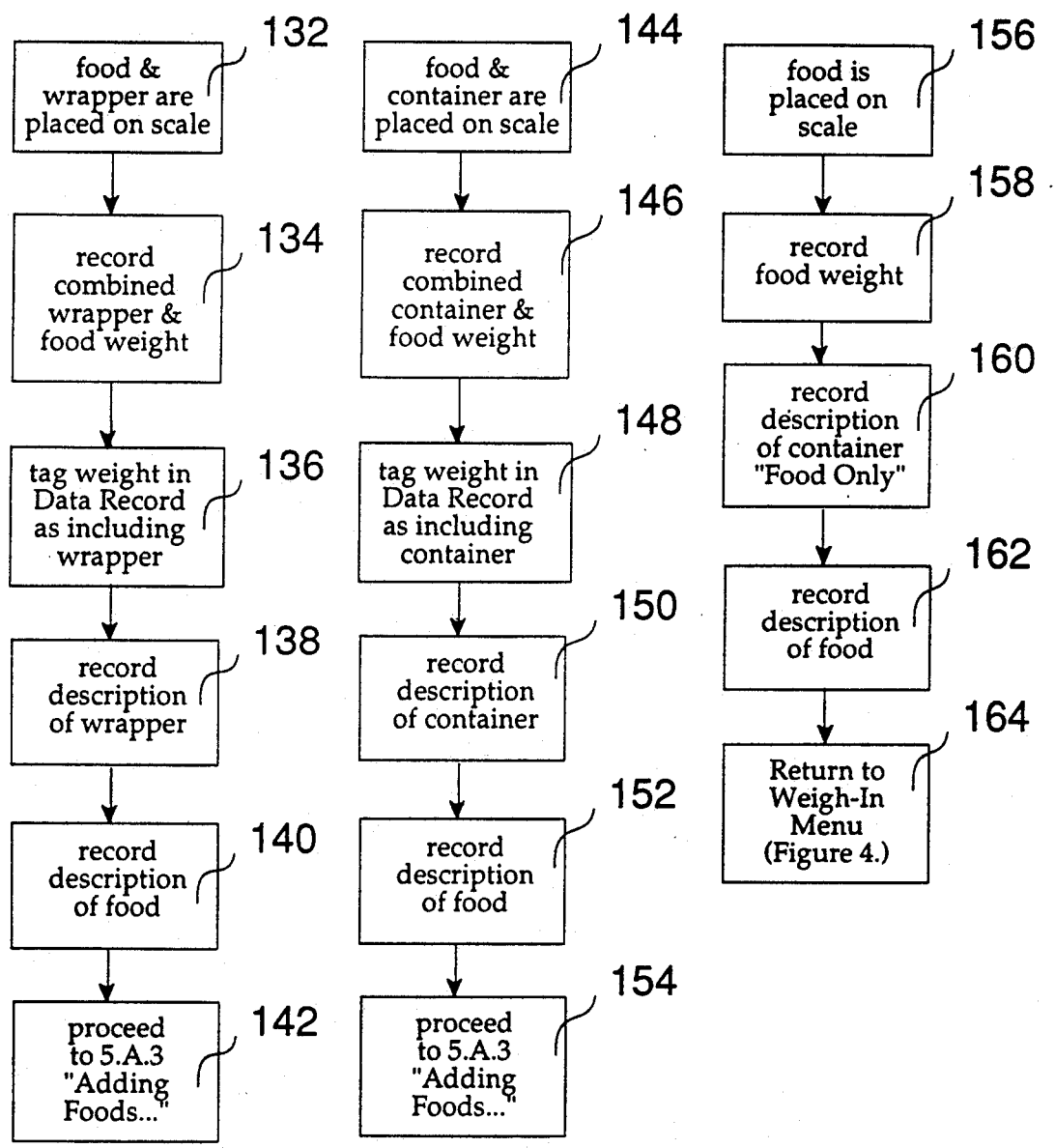

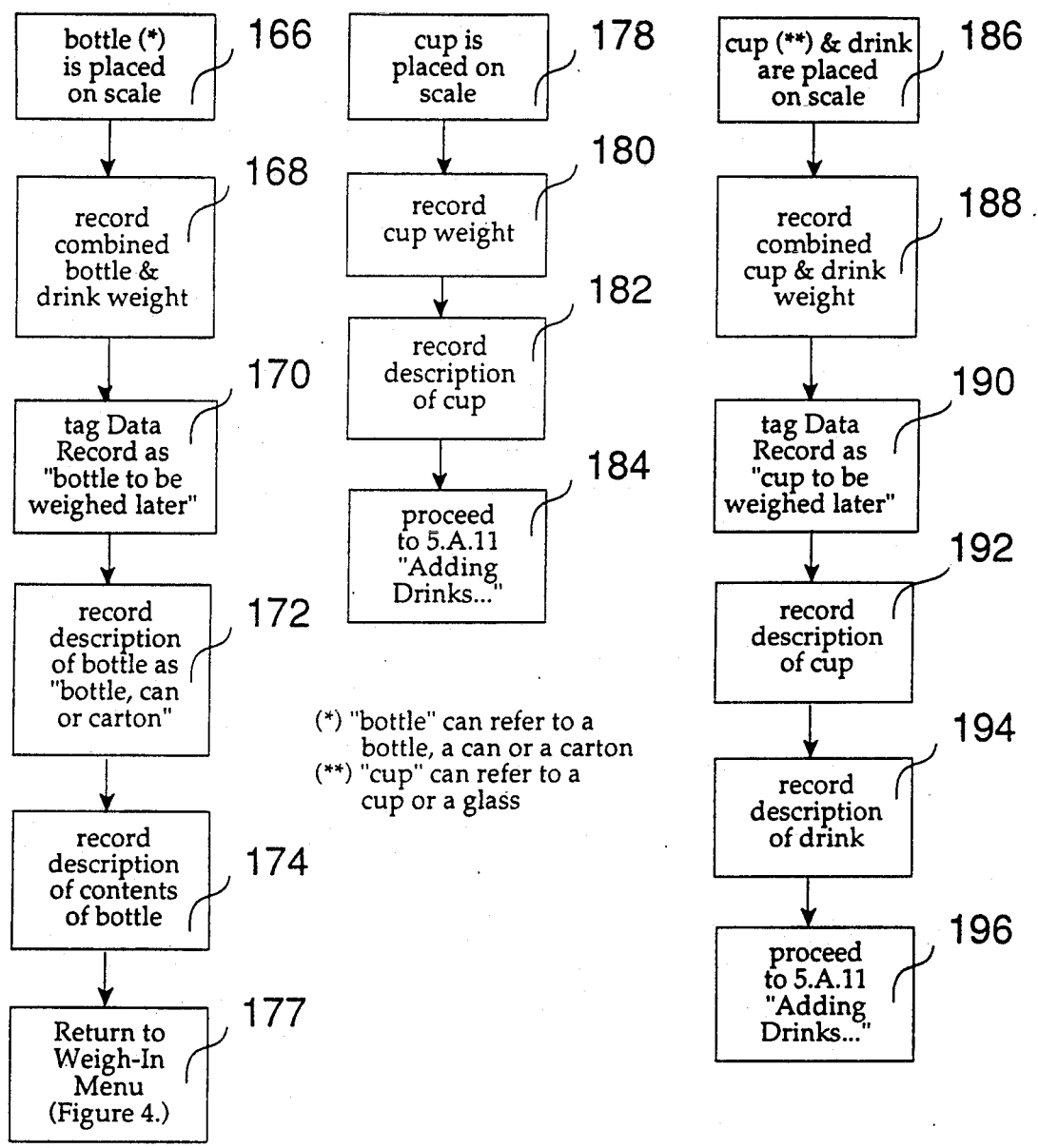

5.A. Individual Intake Food Weigh-In Methods
5.A.10 Ice (Only) in Cups
5.A.11 Adding Drinks to Cups
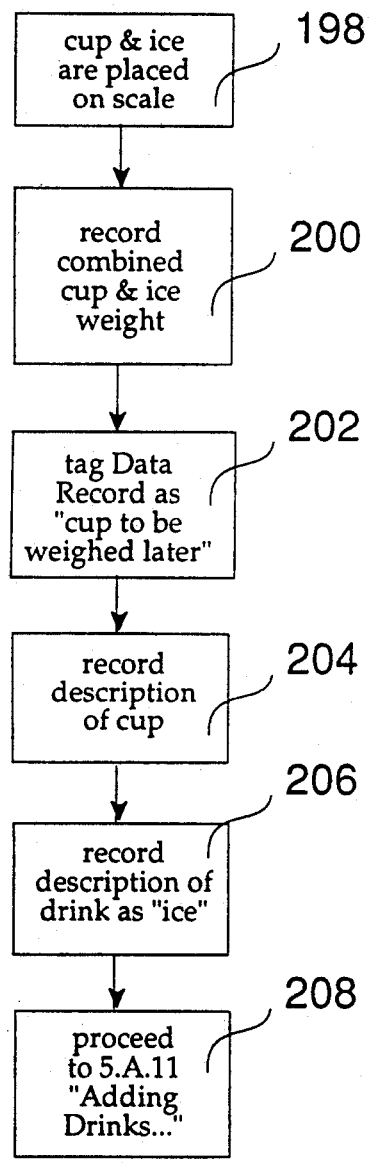
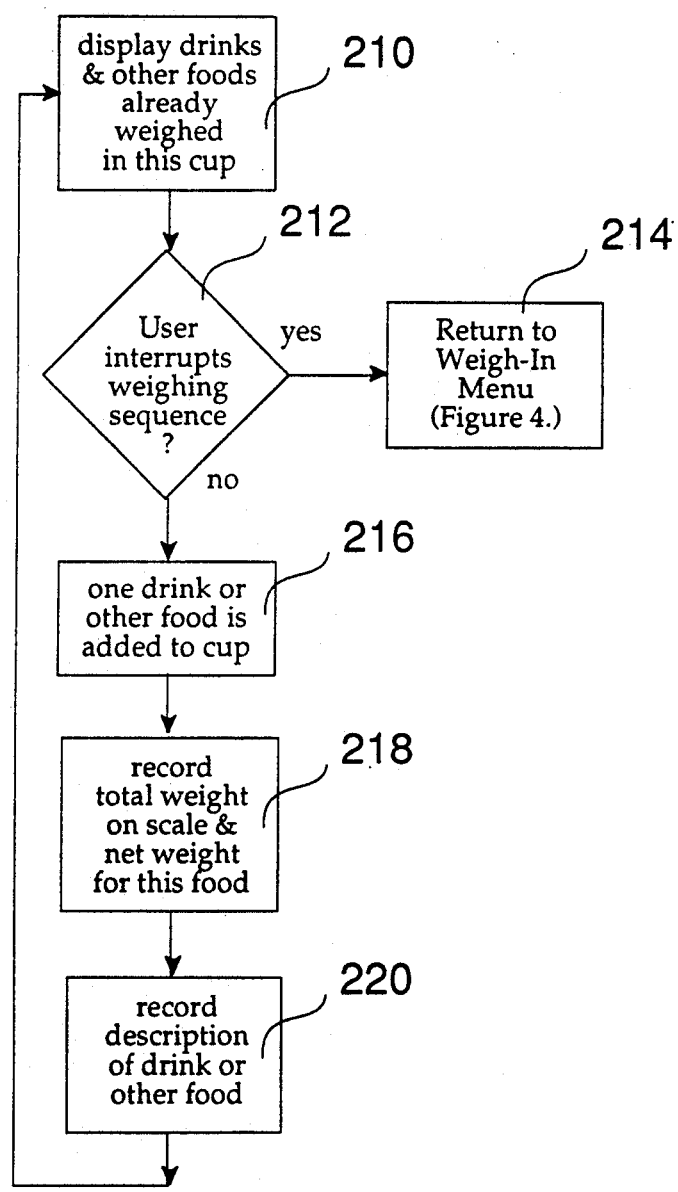

5.A. Individual Intake Food Weigh-In Methods
5.A.12 Second Helpings to Food Already Weighed In
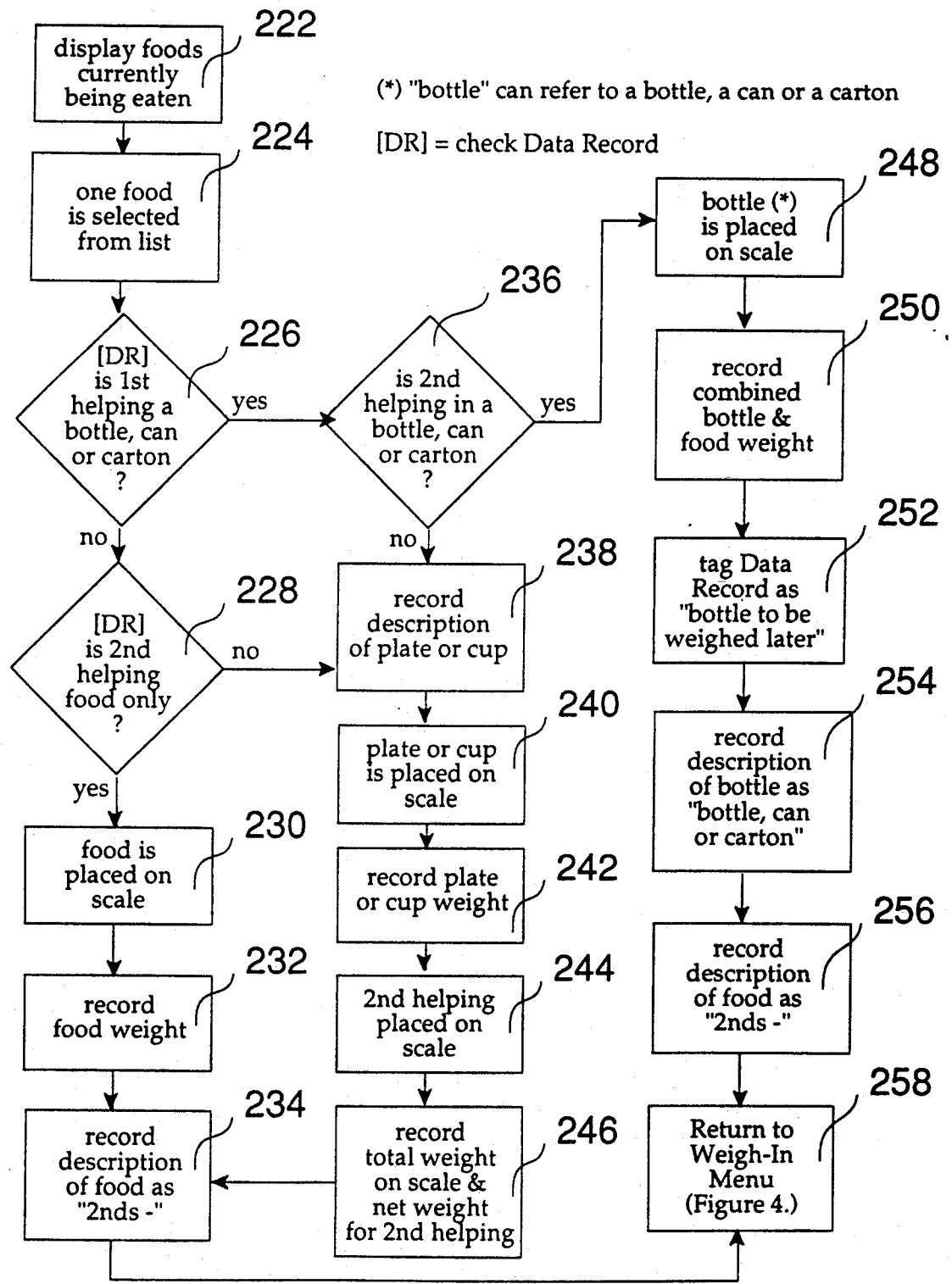

5.B. Bulk Food Weigh-In Methods
5.B.1 Ingredients
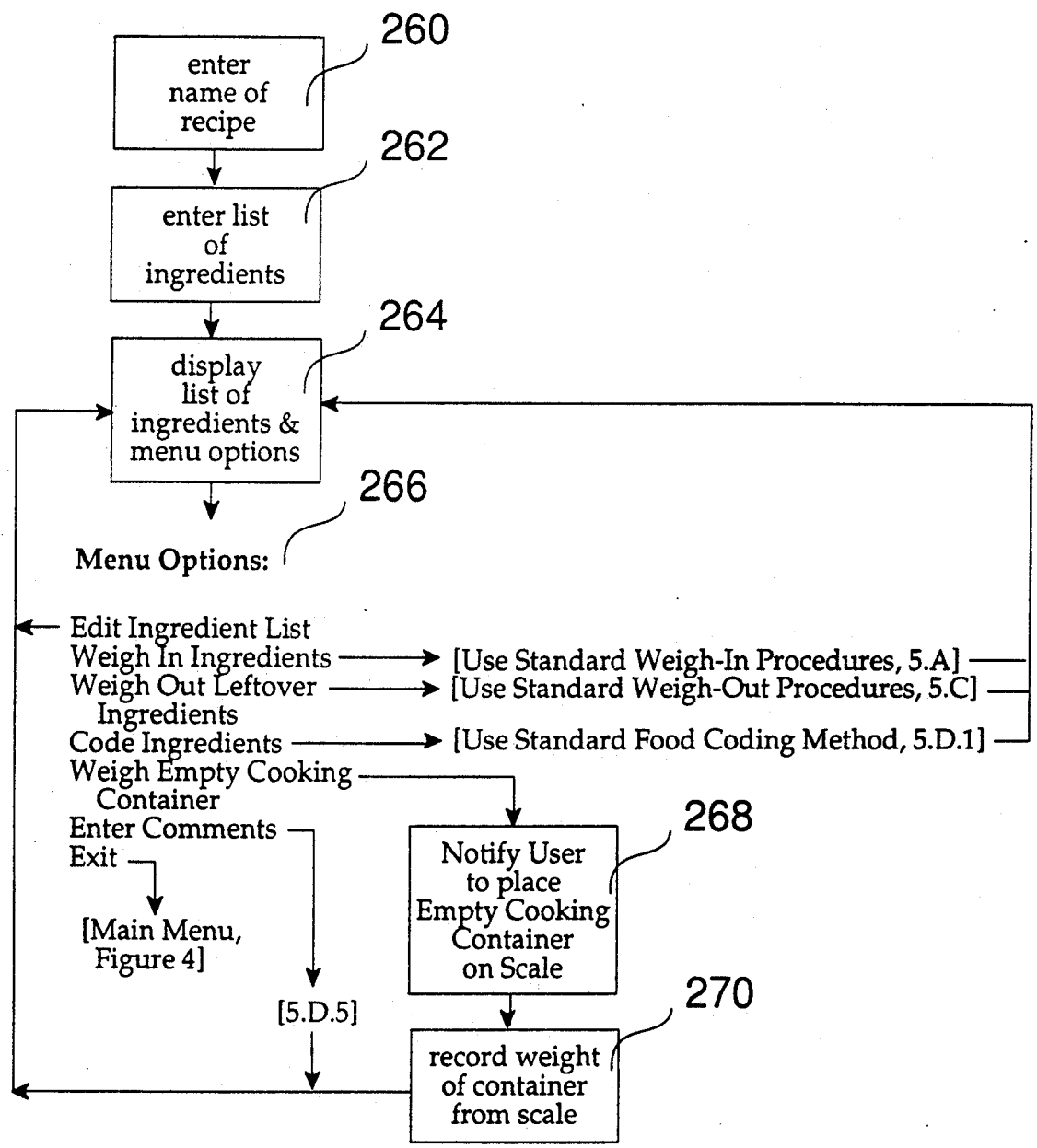

5.B. Bulk Food Weigh-In Methods
5.B.2 Final Recipe Weights
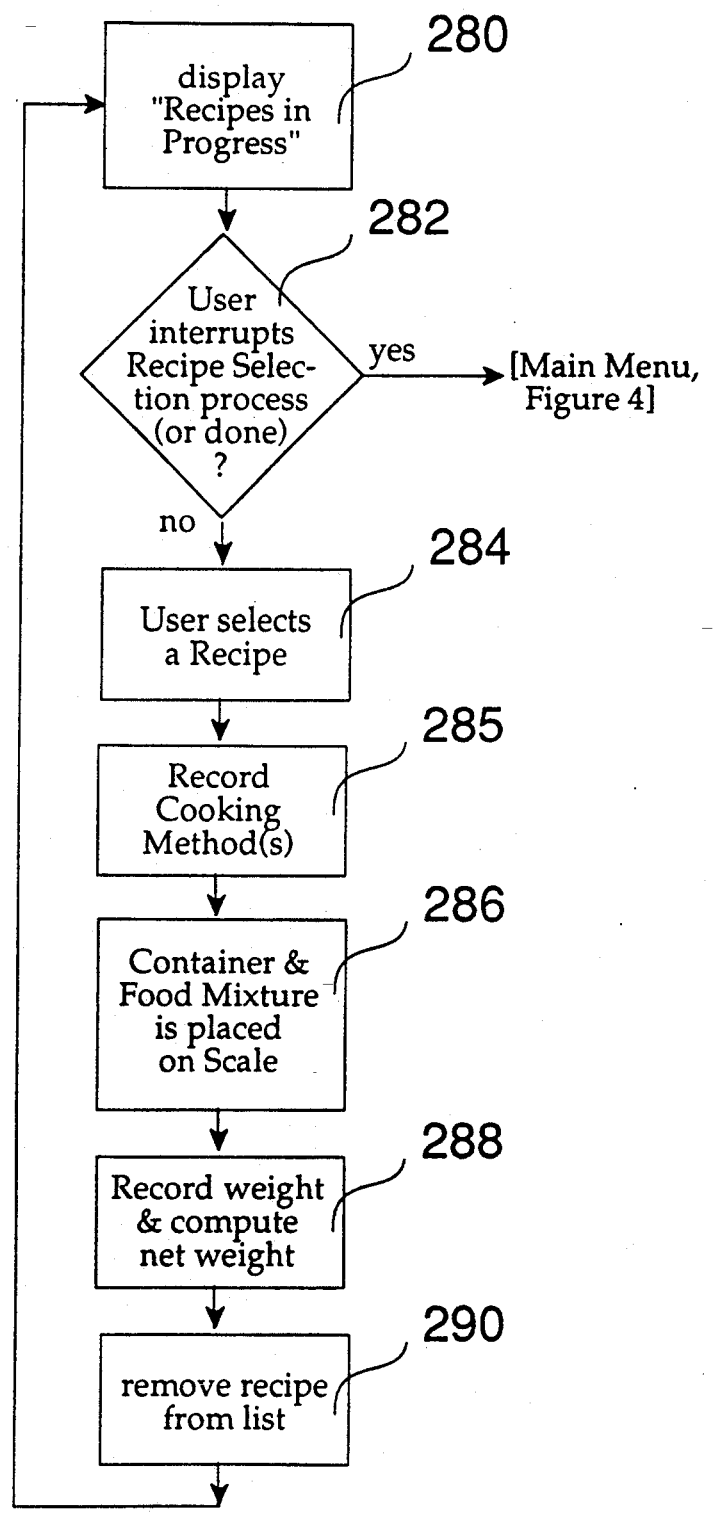

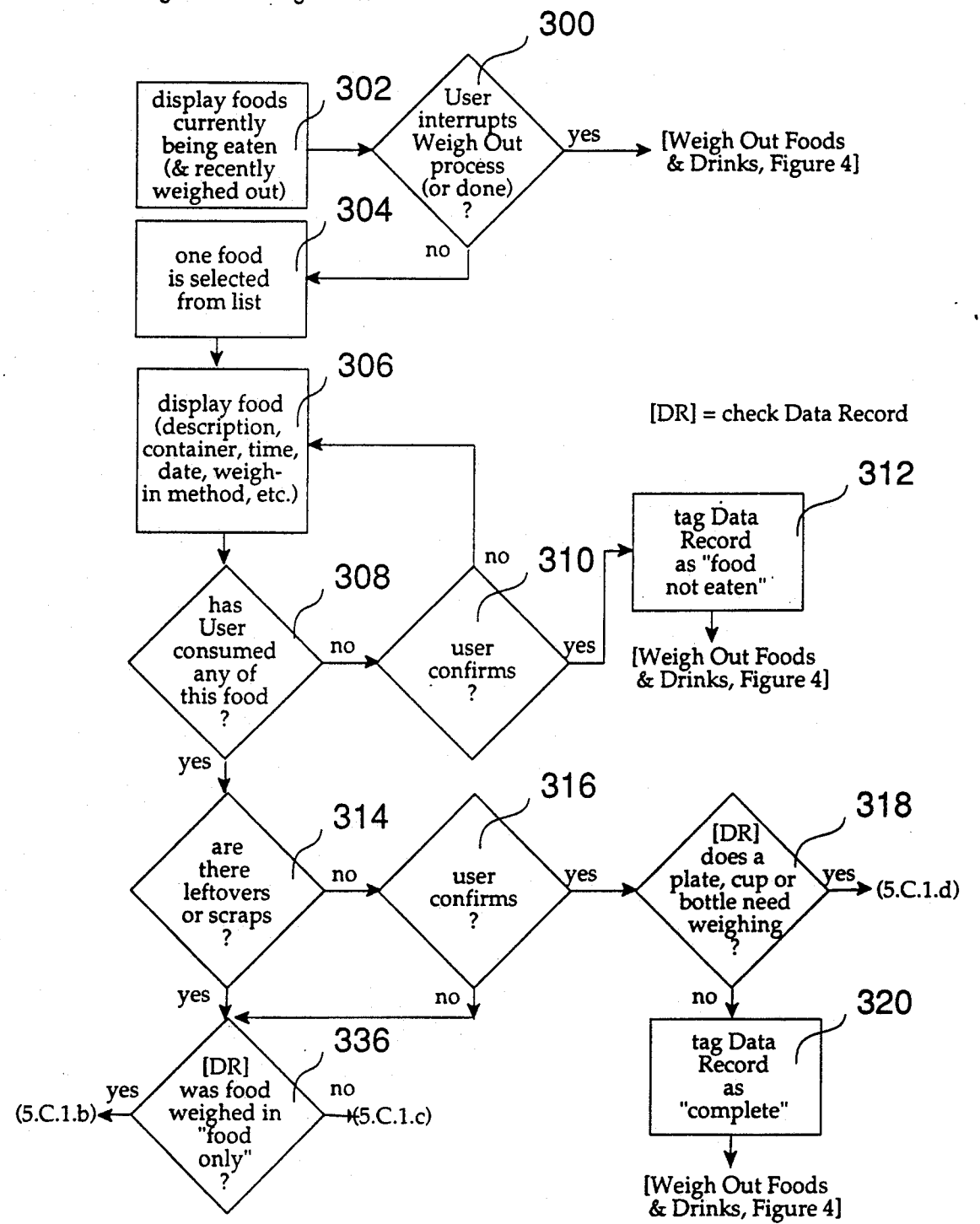
5.C. Individual Intake Food Weigh-Out Methods
5.C.1 Single Food Weigh-Outs

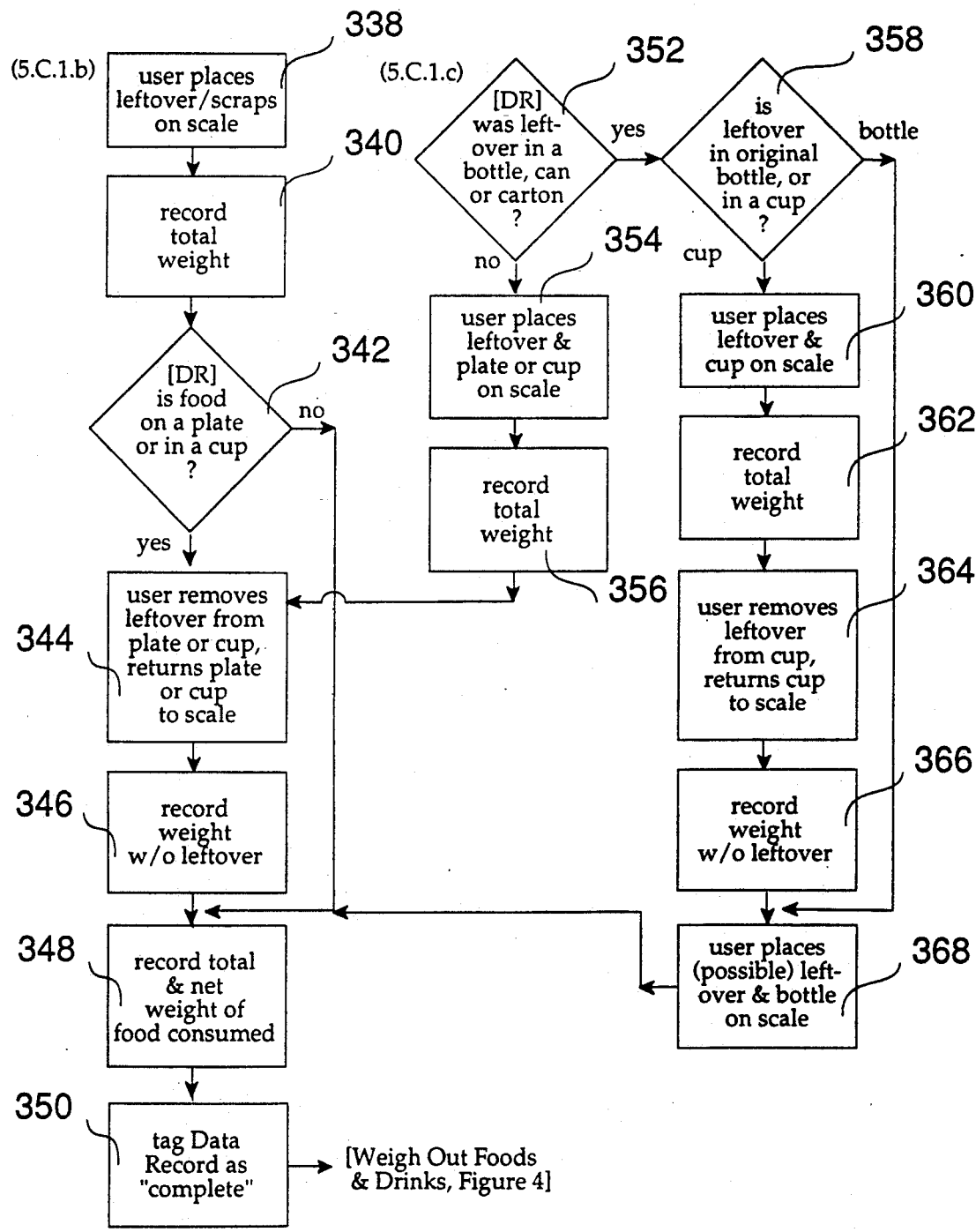

5.C. Individual Intake Food Weigh-Out Methods
5.C.1 Single Food Weigh-Outs (Cont'd)
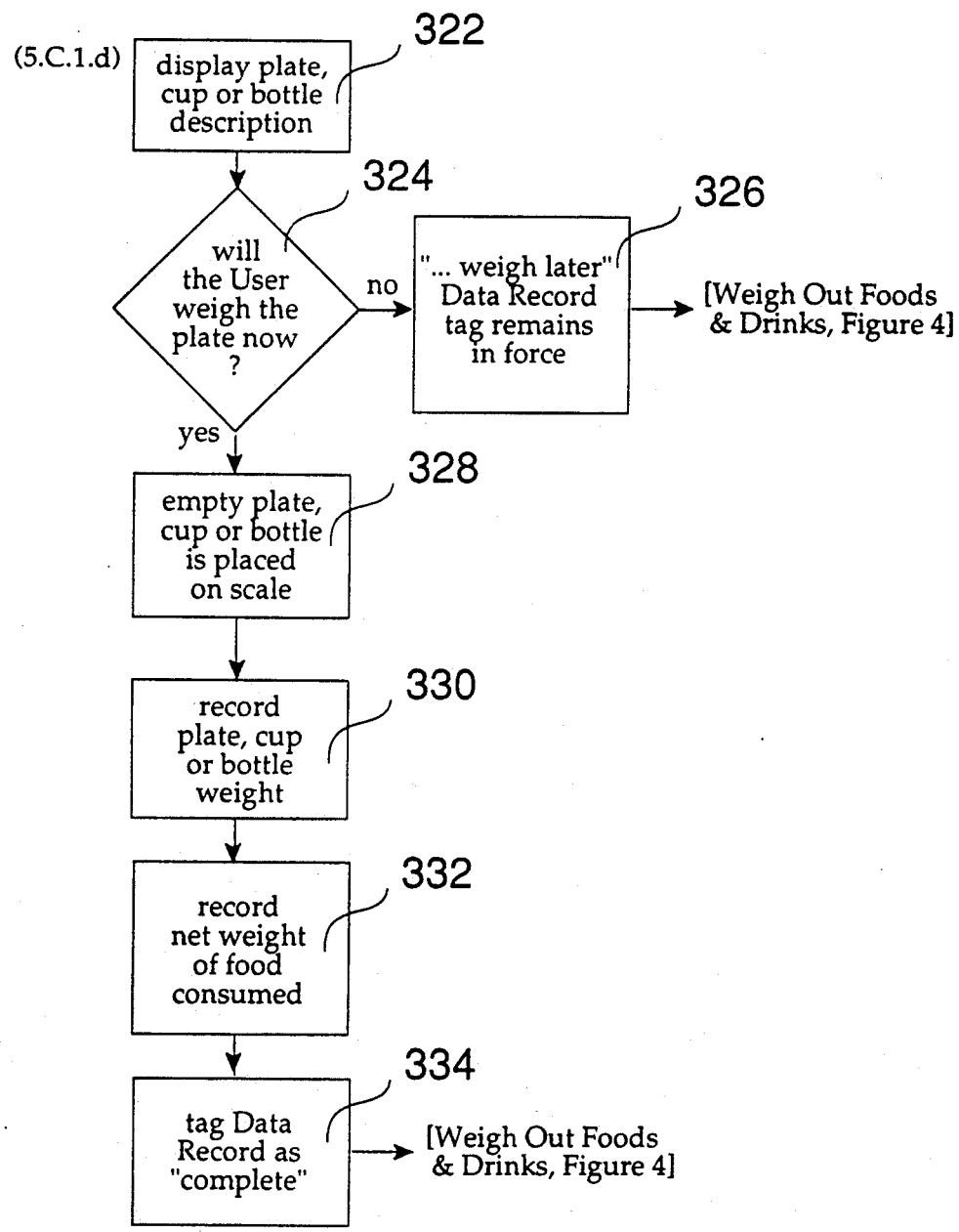

5.C. Individual Intake Food Weigh-Out Methods
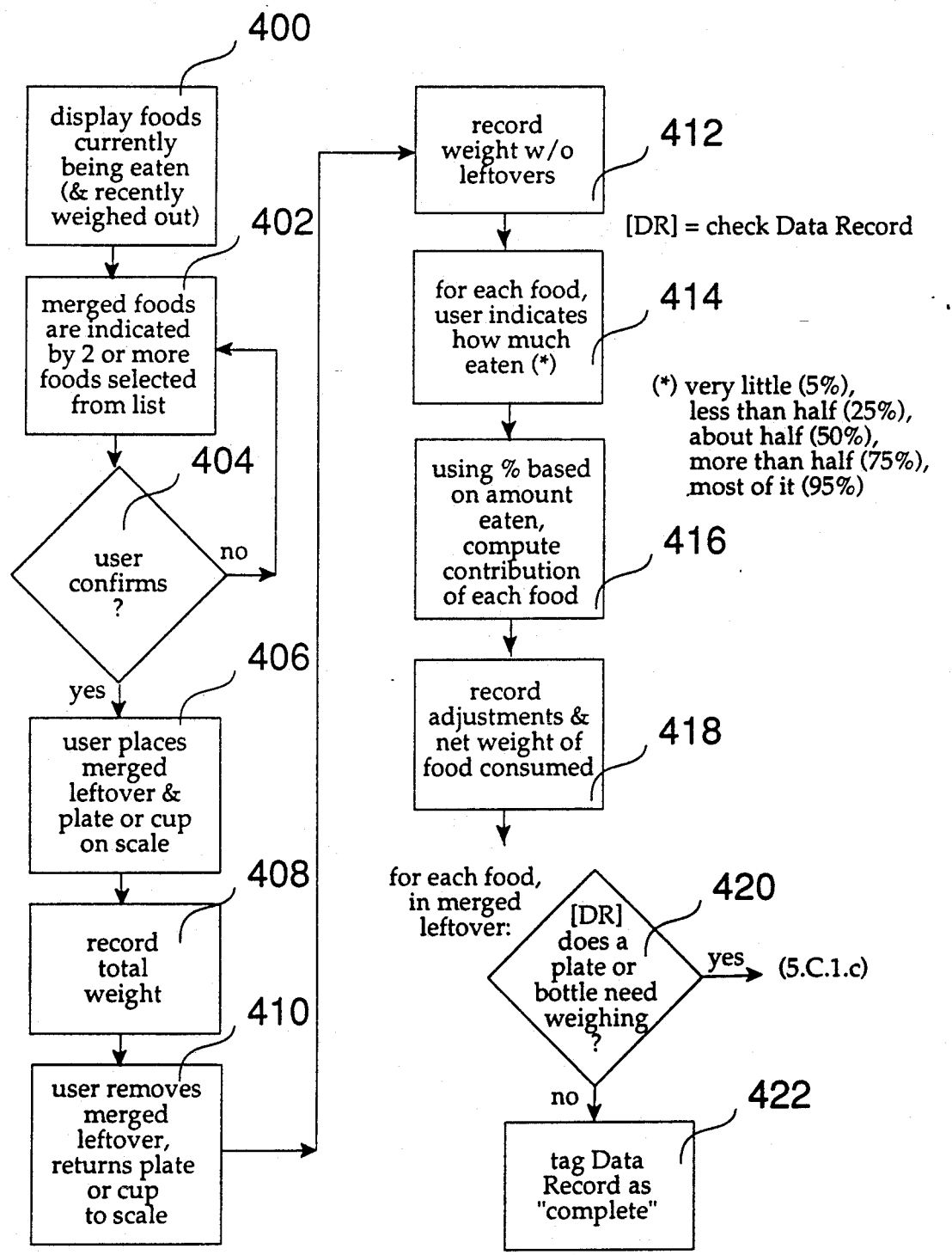

5.C. Individual Intake Food Weigh-Out Methods
5.C.3 Unweighed Plates, Cups and Bottles
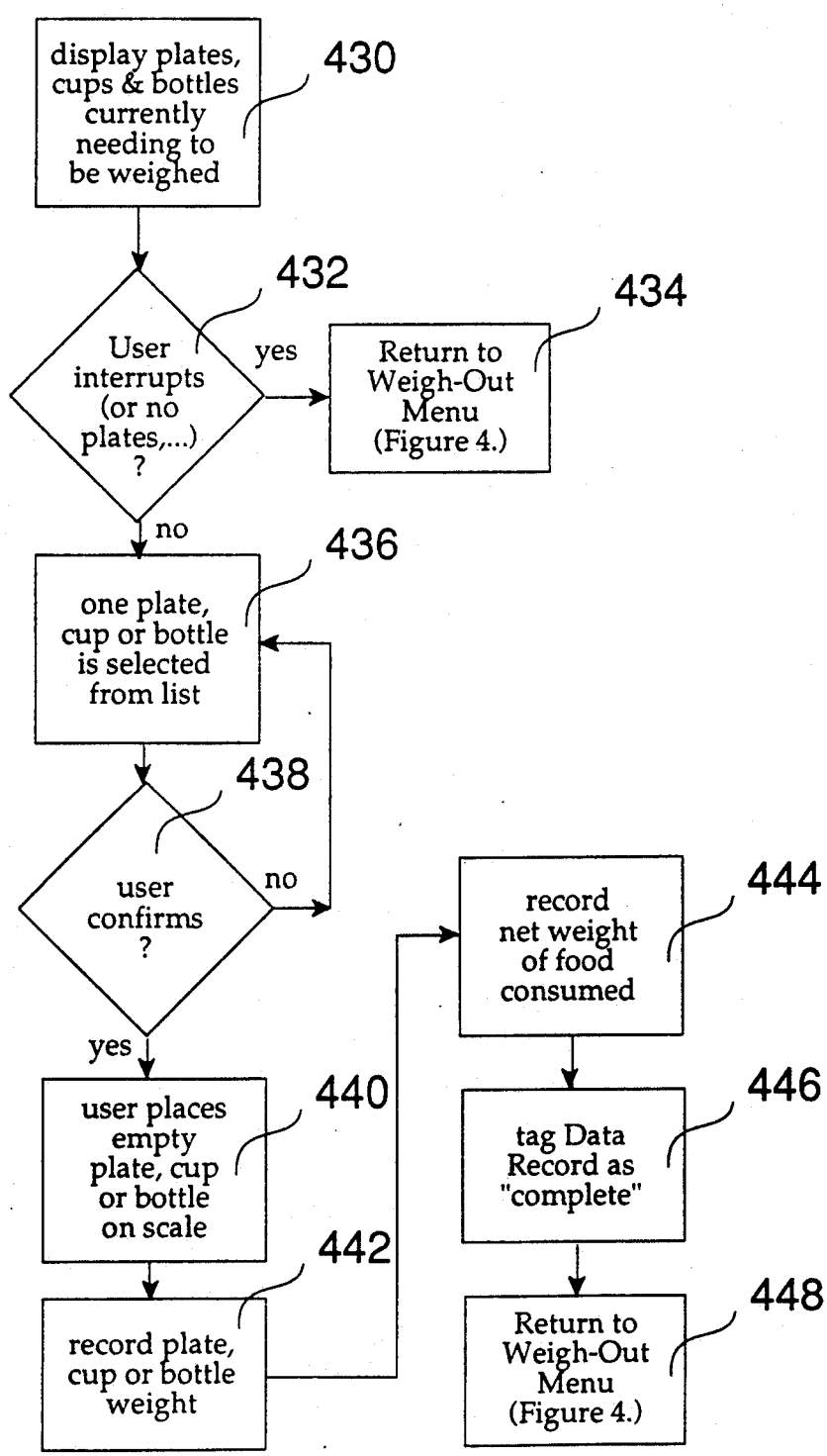

5.C. Individual Intake Food Weigh-Out Methods
5.C.4 Spills
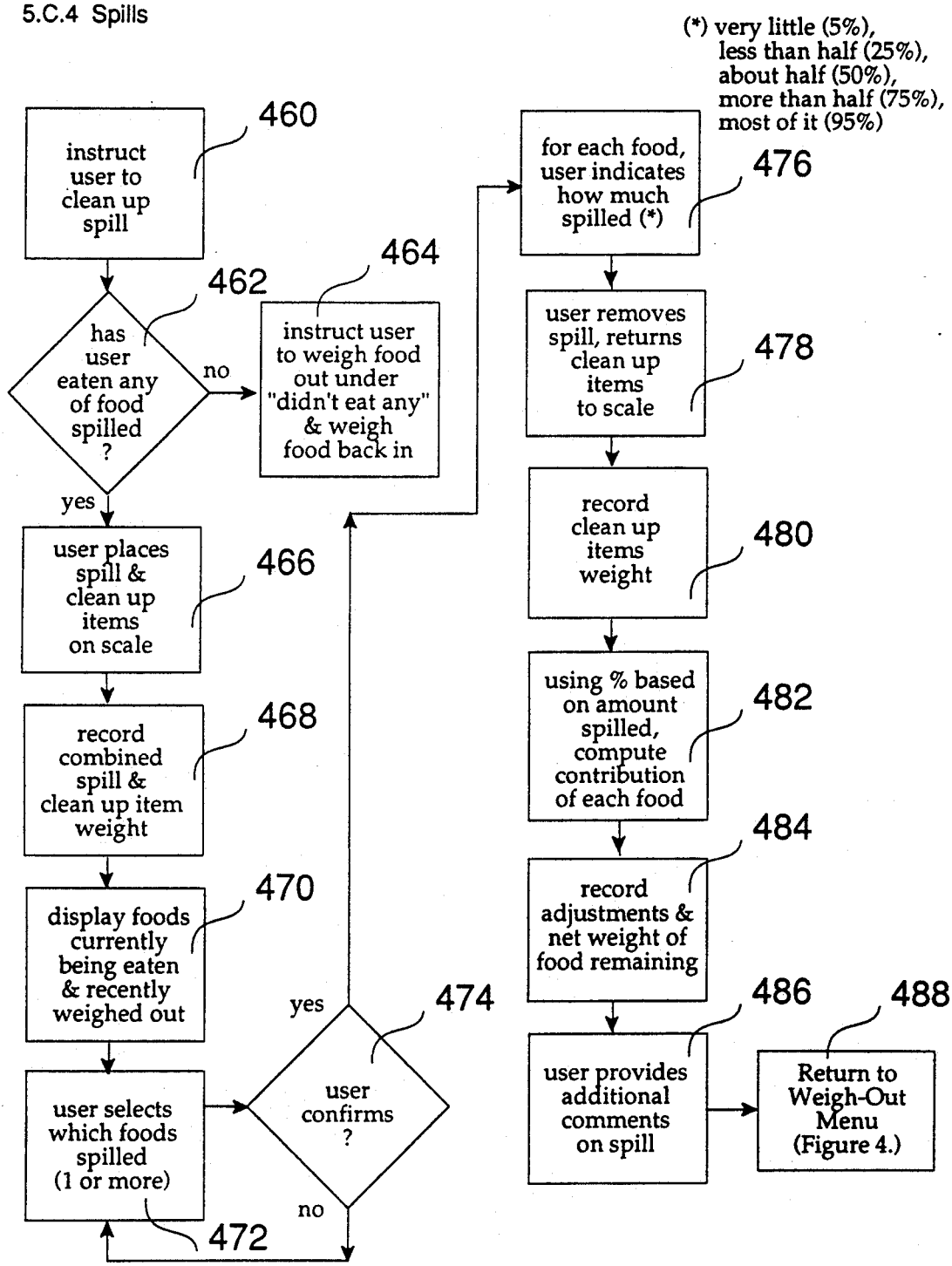

5.C. Individual Intake Food Weigh-Out Methods
5.C.5 Forgotten Items
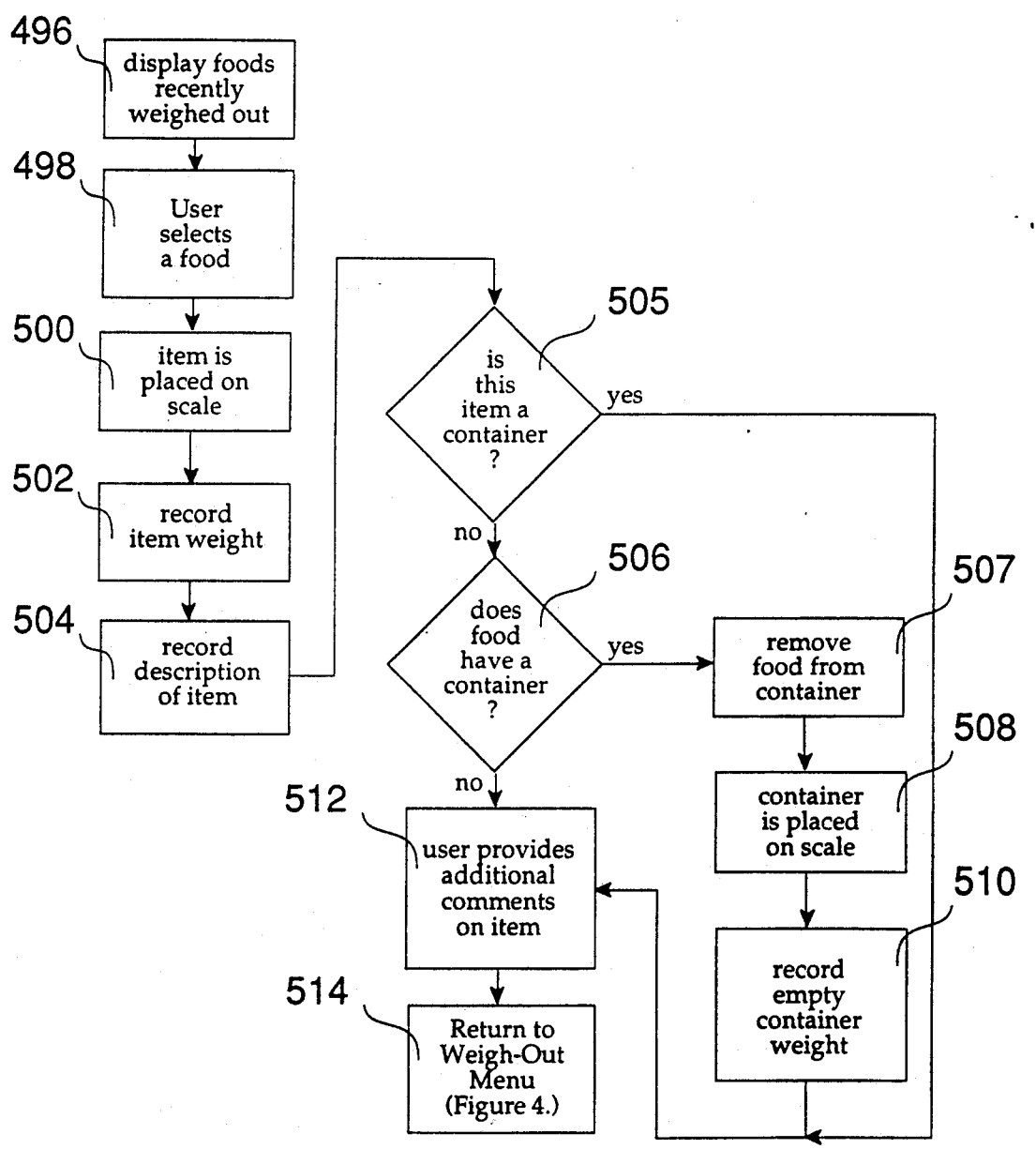

5.D. Special Data Collection Methods
5.D.1 Food Coding Methods
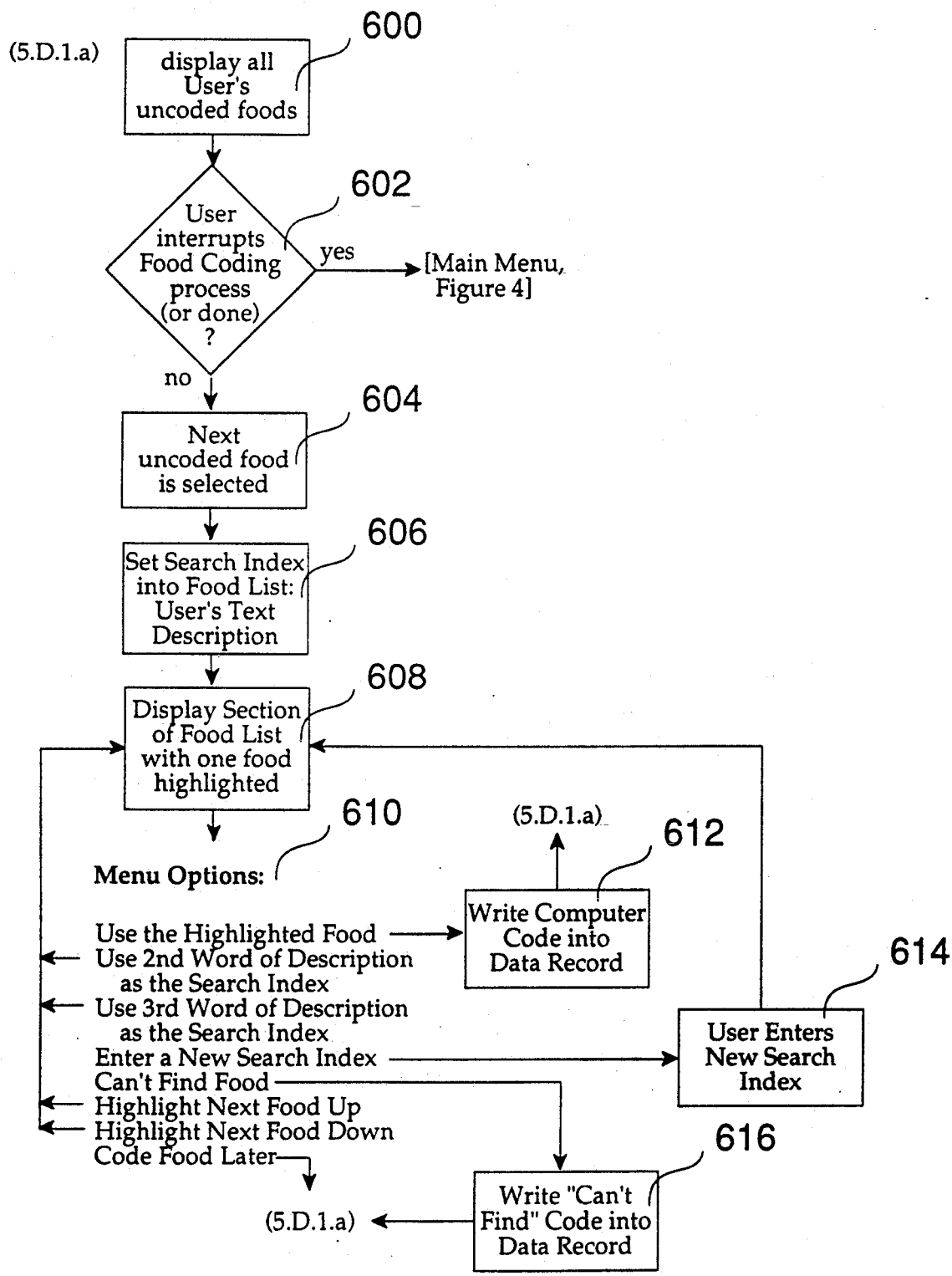

5.D. Special Data Collection Methods
5.D.2 Handling Very Small Weights
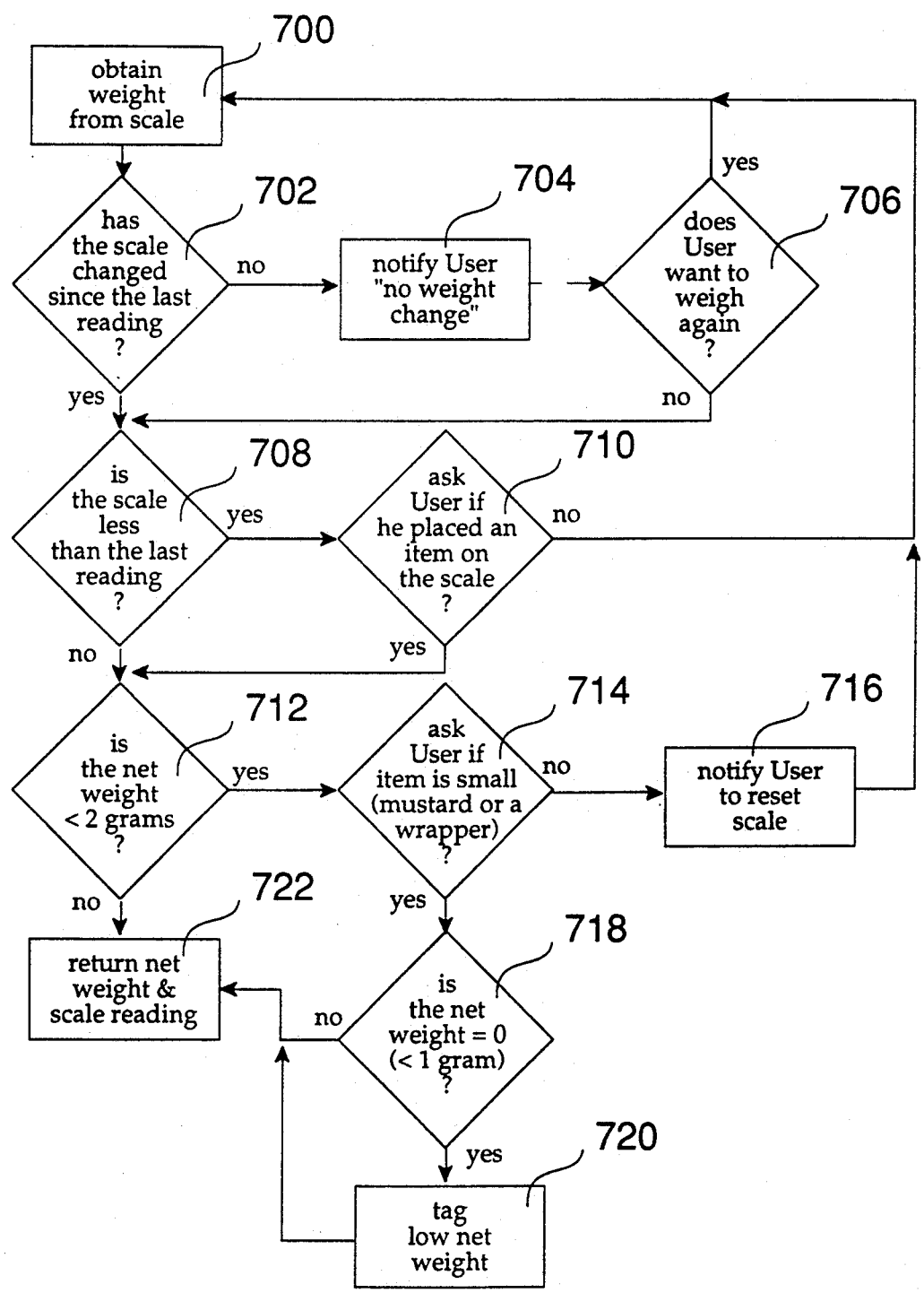

5.D. Special Data Collection Methods
5.D.3 Enabling Multiple Sources for Scientific Food Data
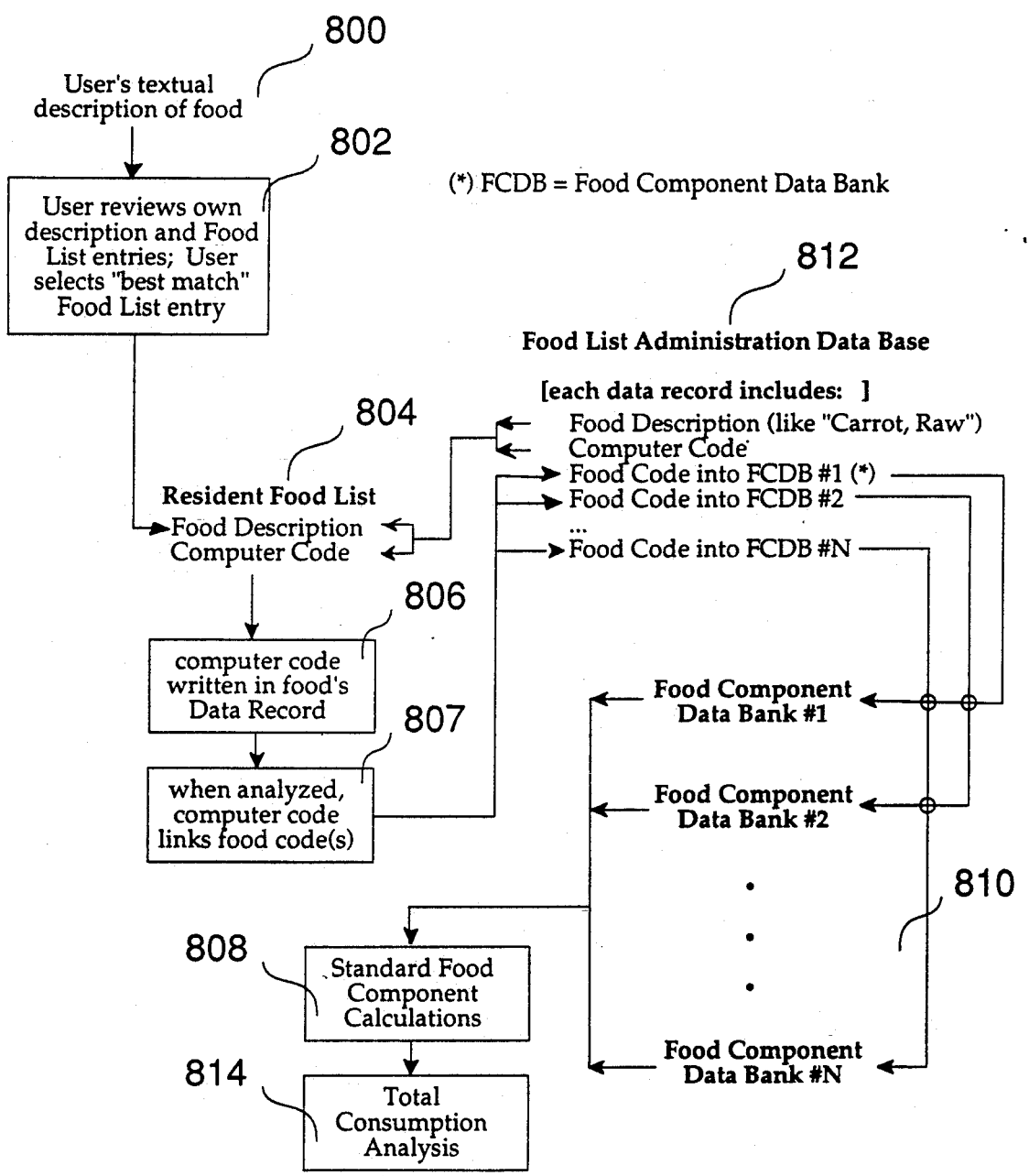

5.D. Special Data Collection Methods

5.D.4 Enabling Accurate Use by Groups with Differing Reading Levels, Languages, Technical Skills and Socio-Economic Backgrounds

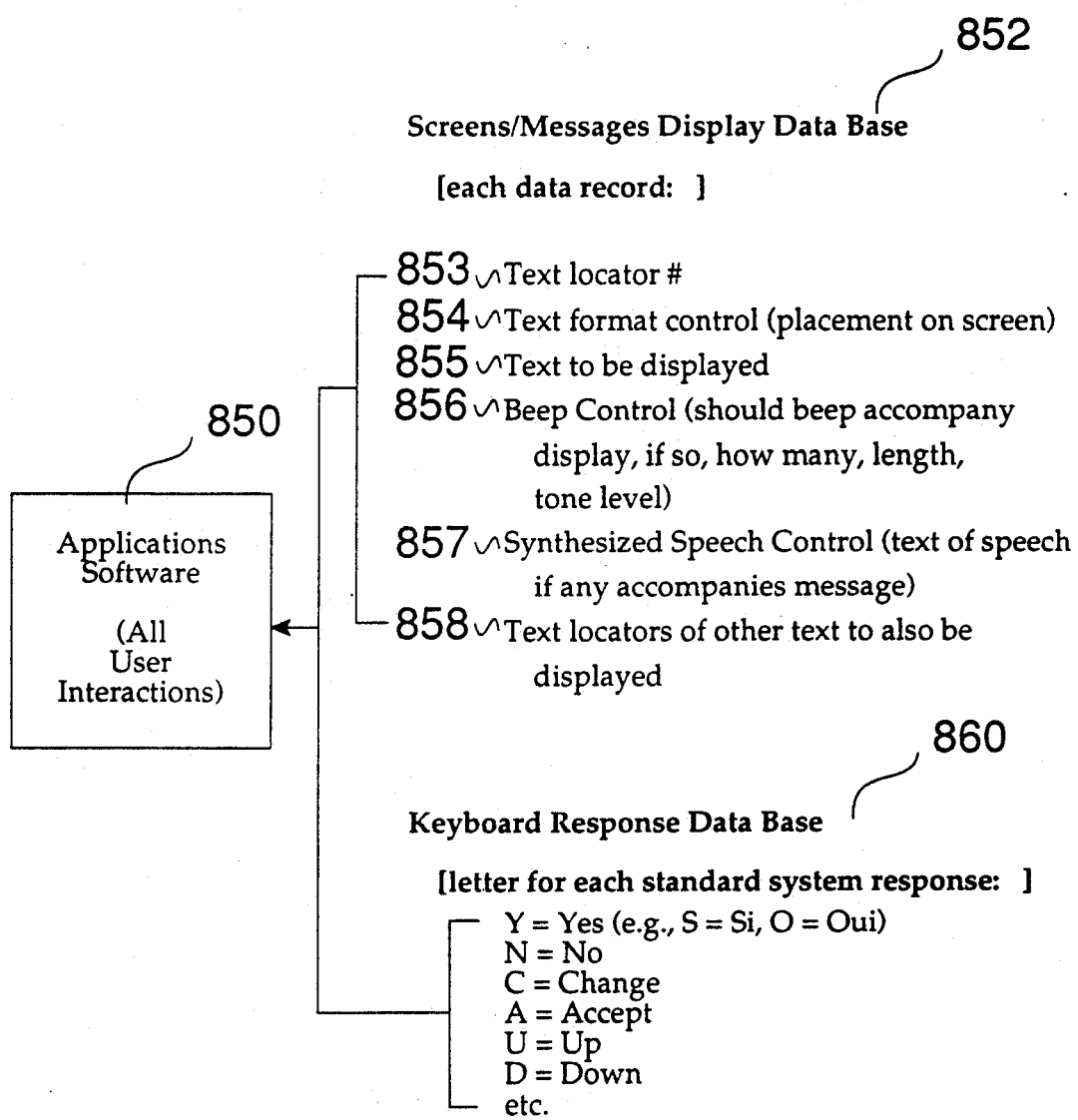

852 Screens/Messages Display Data Base

[each data record: ]

- 853 — Text locator #
- 854 — Text format control (placement on screen)
- 855 — Text to be displayed
- 856 — Beep Control (should beep accompany display, if so, how many, length, tone level)
- 857 — Synthesized Speech Control (text of speech if any accompanies message)
- 858 — Text locators of other text to also be displayed

850 Applications Software (All User Interactions)

860 Keyboard Response Data Base

[letter for each standard system response: ]

- Y = Yes (e.g., S = Si, O = Oui)
- N = No
- C = Change
- A = Accept
- U = Up
- D = Down
- etc.

5.D. Special Data Collection Methods
5.D.5 Collection of User Comments
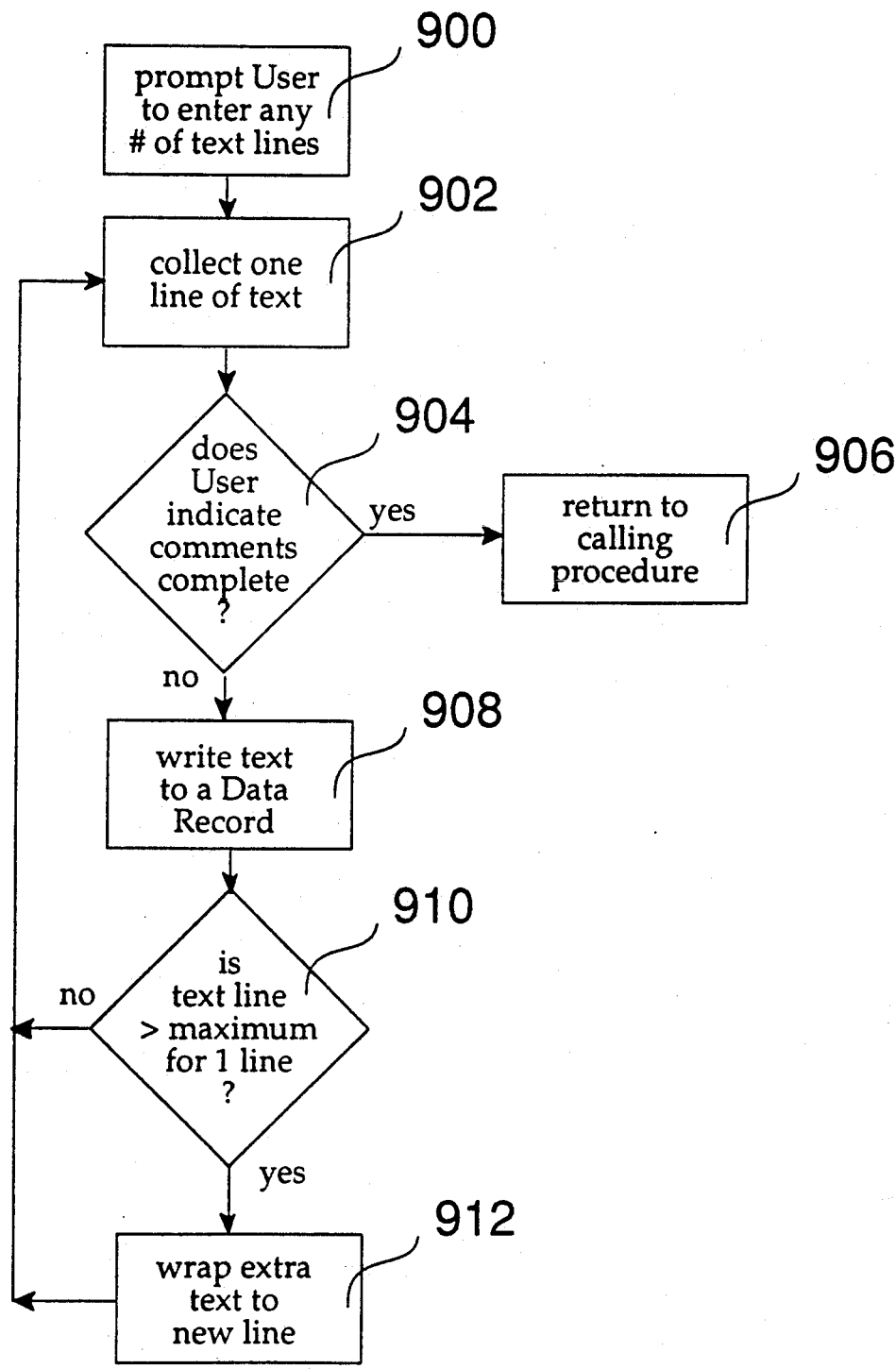

METHOD AND SYSTEM FOR MEASUREMENT OF INTAKE OF FOODS, NUTRIENTS AND OTHER FOOD COMPONENTS IN THE DIET

BACKGROUND OF THE INVENTION

1. Field of the Invention

This invention relates to an interactive computerized system and process which can be used by lay people for accurate measurement of the intake of foods, nutrients and other food components in the diet.

2. Description of the Art

The substantial impact of daily dietary patterns on the health of Americans is now a well-recognized fact throughout our nation. In recent years, scientific investigations have produced abundant information on the ways dietary eating habits can affect health. As summarized in *The Surgeon General's Report on Nutrition and Health* (United States Department of Health and Human Services, Washington, D.C. 1988), ". . . what we eat may affect our risk for several of the leading causes of death for Americans, notably, coronary heart disease, stroke, atherosclerosis, diabetes, and some types of cancer." Since 1936, the U.S. Department of Agriculture has been responsible for conducting periodic surveys of food consumption. Currently, the agency's Nationwide Food Consumption Survey includes information on individual dietary intake, which serves as a basis for determining the magnitude of inadequate or imbalanced nutrition in the general population. Unfortunately, most methods used for dietary assessment are not scientifically based.

Numerous methods exist for measuring dietary intakes of individuals and of groups of individuals. Some are relatively simple, rough estimates, while others are more quantitative measures of food eaten. In most cases precise weighing methods demand close supervision of participants involved in the diet study or the actual weighing is done by dietitians or trained dietary assistants. Because of the labor and time costs associated with the more accurate data collection techniques, few studies and surveys employing dietary assessment have obtained accurate, quantitative data. In addition, the length of time spent on data processing of manually collected information is a concern for many researchers. Such processing work includes: coding of food records, verification of the coded work, manual computer entry of the coded information, and verification of the accuracy of the entered data. This data processing time has been responsible for substantially delaying the reporting of up-to-date food intake information. As a result, decisions on national health policy related to food and nutrition, national dietary recommendations, and national food programs (such as, the School Lunch and Food Stamp programs) have been hindered due to a lack of accurate and current dietary intake information.

Microcomputer nutrient calculation software programs, such as "Nutritionist III" (N-Squared Computing, Salem, Ore.) and "The Food Processor" (ESHA Research, Salem, Ore.), have been used by professionals in the field of nutrition and dietetics for calculating nutrient intake. Although there is computerization of the labor involved in some aspects of the food record coding, processing, and nutrient conversion, such software programs have not computerized the human effort involved in obtaining food intake weights. These nutrient calculation programs primarily have been designed to analyze recipes, meals, and diets using estimated food intake weights. The estimated food intake weights are usually derived from recalled amounts based on human memory or written estimates of foods eaten. Thus, the limitations of such software are in 'how' the food intake information was gathered and in the 'magnitude' of manual labor involved in the collection and entry of the intake data.

For the lay person who is interested in food and nutrition, commercial dietetic computer scales are available. Such units like the "Sentron Health Scale", "Sunbeam NutriScale II" and the "Polder Dietetic Computer Scale" are sold on the open market in the U.S. as tools for weight-loss or dietetic control regimes. Limitations of these domestic kitchen nutrient computing scales include: they are designed for single user application in monitoring specific nutrient intake, they are unable to intelligently interface with the user or other electronic equipment and instead rely on the user to remember all food weighing steps and procedures, they are limited to a pre-determined list of foods with a limited number of accompanying nutrients, their memory capacities are small and do not allow for retention of data over long periods, they are unable to quantitate mixed leftovers, spills, or foods consumed away from home, and because they are designed to provide a quick nutrient report of the foods to be eaten, the output contains limited nutrient information. They are simply data containing calculators designed to compute limited nutrients for a limited number of foods.

On a slightly more advanced end, the Food Recording Electric Device, denoted as FRED, (L. Stockley et al., *Human Nutrition: Applied Nutrition* 40A: 13–18, 1986) uses computer technology for collecting dietary information in the home. FRED consists of a pair of electronic scales interfaced to a microprocessor control unit with an RS-232 communications port. The surface of the control unit consists of an upper bank of six sequence control keys (e.g. 'start', 'waste', 'no waste', 'mixed waste', and 'done') and four colored sequence lights, and a lower bank of 55 "food group" record keys, all of which are color coded. The sequence lights act as prompts indicating the color of the key which is next in the sequence.

The major disadvantage of FRED as a computerized food weight method is that it does not have an intelligent man-machine interface. The software and hardware limitations of FRED prohibit FRED from providing the user with prompts and directives for food intake weighing and recording and prohibit the user from providing alpha-numeric response and descriptive information to FRED. Since FRED is non-interactive, it relies on the ability, the memory, and the intelligence of a human operator to understand the action messages embedded in the color sequence, to synchronize human action with light prompts which are in a color sequence, and to be capable of separating food names into "food group" categories in order to press the correct "food group" button during food identification operations. Because the user must control the actions of FRED rather than FRED controlling the actions of the user, data accuracy and reliability are questionable.

Other disadvantage of FRED include: each unit was designed for single user rather than multiple user applications; it does not provide for flexibility in the eating habits of users in that only one food weighing routine is available; it does not have a means to quantitate mixed leftovers, spills, or foods consumed away from home; it does not keep track of the containers used to weigh food thus increasing the likelihood of food weight errors; it does not have a means to detect errors made during the food weighing process; it is not capable of gathering from the user data other than food weights and "food group" identifications; food identifications are limited to the 'food group' classifications provided by the researcher; only energy, protein, and fat intake can be calculated from the FRED food groups; the food identification limitations restrict usage of the data to nutrient intake estimation of populations, i.e. nutrient intake of an individual is not accurate; and the capability to calculate nutrient consumption information is not resident on FRED. There were plans to expand FRED's "food group" system to 104 "food groups" and to cover carbohydrate, sugars, starch, and dietary fiber in the nutrient analysis, however, to the best of our knowledge no new literature has been published nor have upgraded FRED models been announced.

SUMMARY OF THE INVENTION

As a response to the need to move beyond limitations of current dietary assessment methodology, the Nutrition Evaluation Scale System (NESSY), a new system and process to gather dietary intake information, was designed and developed to ensure that: the process of dietary information assessment is based on scientifically valid parameters; the most accurate and up-to-date food, nutrient, and dietary component intake information is provided; the simplicity and flexibility necessary to enable use by the general public is provided; and substantial labor, time and cost savings are realized when compared against other quantitative dietary assessment methods.

This invention has application in the fields of Nutrition and Dietetics as well as all related fields which utilize dietary and/or nutritional status assessment methodology, i.e., Agricultural Economics, Public Health, Medicine, Dentistry, Epidemiology, Anthropology, Exercise Physiology, and Individual Health Care. Individual health applications encompass dietary monitoring and nutrition education for weight loss, diabetes, heart disease, hypertension, as well as any health status positively or adversely affected by diet.

The logical extension of the computer revolution is to use the computer to intelligently and interactively collect, process, and summarize dietary information in the home. NESSY is the all encompassing system specially designed to perform such specified tasks.

The present invention discloses a novel system and process for accurately, rapidly and easily determining the food, nutrient, and food component intake of individuals. NESSY, which is an acronym for Nutrition Evaluation Scale System, is a computerized interactive system and process which can be used by lay people for the input, storage, calculations, output and data transfer of food intake data. The system of the invention can generate accurate food intake data in electronic form through the capabilities of:

(a) automatically recording food and container weights, without error, to the accuracy permitted by the electronic balance, (b) signaling weighing errors and enabling corrective actions, (c) enabling a variety of ways in which to weigh-in foods including foods with containers; drinks in containers, bottles, cartons or cups; pre-packaged foods; foods with no containers; multiple foods served on a single plate; drinks with solid foods or ice added; foods from a food list; and second helpings of food, (d) tracking food that is being eaten, (e) tracking containers that are in use, (f) enabling a variety of ways in which to weigh foods out, including the handling of merged leftovers and spills, (g) enabling automatically recording of food and container weights, without error, for food mixtures and the components of the mixtures, (h) collecting comments from the user, (i) enabling a number of people to utilize a single system, (j) linking food items to multiple nutrient and/or dietary component data banks, (k) enabling easy changes to speech and visual output including changes to accommodate foreign languages, technical skills, ethnic and regional differences and readability levels within the same language, without changes to the system and process, (l) collecting food recall data and food eaten away from home, (m) optionally transferring data via telephone lines for central collection and/or further processing, (n) optionally verifying items weighed in and out through synchronized video images.

One important advantage of the invention is the provision of a means for rapidly and easily determining the intake of food and dietary components at a level of accuracy commensurate with the current "gold standard" of dietary methodology, which is the weighed food record measured by trained dietetic staff. Use of the invention enables a lay person to collect dietary data at the level of accuracy previously possible only with trained professionals. Accuracy is enhanced through:

(a) simplifying and reducing the number of steps necessary to perform a standard weighed food intake procedure, (b) identifying the true amount of food intake through the automatic recording of actual food and container weights, (c) minimizing human error in the identification of foods, (d) providing time and date tracking data for each data entry, and (e) providing full on-screen guidance for the user to perform the necessary steps required.

Another advantage is the transfer of labor from the professional to the lay person, thus enabling substantial cost savings. The labor transfer is possible because the system's design allows for ease of learning and ease of operation.

Another advantage is the reduced labor requirement needed for dietary data acquisition, calculation, processing, and summarization.

Another advantage is the ability to calculate energy, all nutrients, and all other dietary components (e.g. cholesterol, food additives, toxic elements, pesticide residues, etc.) for which food composition data is available internationally.

Another advantage is the immediate feed back of the individual's nutrient and/or dietary component consumption profile. This enables targeting optimal dietary intake, as well as providing menu planning flexibility for people on restricted diets.

Another advantage is the capability to easily minimize the impact of ethnic, regional, reading level, foreign language, and technical skill differences of the various users on the dietary data accuracy. This feature breaks through language and cultural barriers thus enabling multilingual and multicultural applications.

Another advantage is that through the collection of dates and times, it is possible to examine meal patterns and dietary habits.

Another advantage is the ability to collect accurate food ingredient weights for food mixtures and the components of the mixtures.

Another advantage is the ability to collect the necessary food intake information without the user changing his or her way of serving or eating the food.

Another advantage is the ability to utilize Universal Product Codes from commercial products to uniquely identify foods.

Other advantages and objects of the invention will become readily apparent from the ensuing description.

BRIEF DESCRIPTION OF THE DRAWINGS

FIG. 1 is a schematic diagram of the primary components required for a computerized dietary measurement system in accordance with the present invention.

FIG. 2 is a schematic diagram of the preferred embodiment of the system in accordance with the present invention.

FIG. 3 shows another preferred embodiment of the present invention which includes both the computerized data collection function and the consumption analysis function.

FIG. 4 is a schematic representation of the multi-level options available to the user for interacting with the system of the present invention.

FIG. 5.A.1 is a flow block diagram of the "empty plate" routine which can be used as a start point for weighing-in the food of an individual.

FIG. 5.A.2 is a flow block diagram of the "plate containing food" routine which can be used as a start point for weighing-in the food of an individual.

FIG. 5.A.3 is a flow block diagram of the "adding foods to plates and foods already weighed-in" routine which is used to add additional foods to a food or plate.

FIG. 5.A.4 is a flow block diagram of the "food in a wrapper" routine which can be used as a start point for weighing-in the food of an individual.

FIG. 5.A.5 is a flow block diagram of the "food in a container" routine which can be used as a start point for weighing-in the food of an individual.

FIG. 5.A.6 is a flow block diagram of the "food only" routine which can be used as a start point for weighing-in the food of an individual.

FIG. 5.A.7 is a flow block diagram of the "drinks packaged in bottles, cans or cartons" routine for determining the weight of a packaged drink.

FIG. 5.A.8 is a flow block diagram of the "empty cup" routine which can be used as a start point for weighing in a drink.

FIG. 5.A.9. is a flow block diagram of "drink in cup" routine for determining the weight of a drink contained within a cup.

FIG. 5.A.10 is a flow block diagram of "ice in cup" routine which can be used as a start point for weighing in a drink containing ice.

FIG. 5.A.11 is a flow block diagram of the "adding drinks and/or foods to a cup" routine which is used to add drinks/food to a cup or drink that has been weighed-in.

FIG. 5.A.12 is a flow block diagram of the "second helpings to food already weighed-in" routine for determining the weight of a second helping of a food.

FIG. 5.B.1 is a flow block diagram of the "ingredients" weighing routine for determining the weight and food codes of ingredients used in a recipe, the weight of the empty cooking/mixing container, and the method(s) of cooking.

FIG. 5.B.2 is a flow block diagram of the "final recipe weights" routine for determining the weight of a food prepared from a recipe.

FIG. 5.C.1 is a schematic diagram of the "single food weigh-out" routine for accurately determining the weight of a food eaten by an individual.

FIG. 5.C.2 is a flow block diagram of the "merged leftovers" routine for determining weight of each food eaten by an individual when the leftovers for the foods have been mixed together during the eating process.

FIG. 5.C.3 is a flow block diagram of the "unweighed plates, cups, and bottles" routine for measuring the weight of food/drink containers not previously accounted for in the weigh-in process for the following routines FIG. 5.A.2, 5.A.4, 5.A.5, 5.A.7, 5.A.9, and 5.A.10.

FIG. 5.C.4 is a flow block diagram of the "spills" routine for determining the amount of a food or drink consumed by an individual prior to the spill.

FIG. 5.C.5 is a flow block diagram of the "forgotten items" routine for determining the weight of the leftovers/scraps/containers which were not recorded during the weigh-out process.

FIG. 5.D.1 is a flow block diagram of the "food coding" routine for determining the identity of a specific food using the resident food list.

FIG. 5.D.2 is a flow block diagram of the "handling very small weights" routine for verifying that the weight of an item is truly very small, i.e., two grams or less.

FIG. 5.D.3 shows the linkage of resident food list computer codes to the food codes in the Food Component Data Banks and how this linkage relates to the total consumption analysis for an individual in a preferred embodiment.

FIG. 5.D.4 shows an approach used to address user comprehension differences for the present invention.

FIG. 5.D.5 is a flow block diagram of the "collection of user comments" routine.

DESCRIPTION OF SPECIFIC EMBODIMENTS

| Terminology | |
|---|---|
| Adjustments | Weight changes (positive or negative) which must be made to correctly calculate the true weight of the food consumed |
| Barcode | An array of rectangular bars and spaces that are arranged in a predetermined pattern to represent a numeric code |
| Bottle | A bottle, can or carton |
| Bulk Food | Food mixtures which may or may not be cooked |
| Computer Code | An alpha-numeric code used for linking a food description to one or more food codes |
| Container | A cup, glass, plate, wrapper, bottle, can, carton, plastic bag, or any other inedible packaging that is used to contain or hold foods |

| Terminology | |
|---|---|
| Cooking Container | The final preparation container for a cooked or uncooked food mixture |
| Cup | A cup or glass, usually for drinks |
| Data Record | The collection of information which describes a single food weighed-in and weighed-out by an individual |
| Display | Make information, prompts, and/or instructions visible and/or audible to the user on output devices such as a computer screen, CRT, voice synthesizer, beep/tone mechanism, etc. |
| Drinks | Any liquid food, with or without solid additions (such as ice or sugar) which will mix with the food to produce a "drinkable" mixture |
| Food | Any solid or liquid food |
| Food Code | An alpha-numeric code used for linking a food description to a food component data bank |
| Food Component Data Bank | Any data base which provides food composition information, such as energy, nutrients, toxic elements and pesticide residues, in response to a food code and a weight |
| Food Intake File | A collection of Data Records |
| Food List | A series of food descriptions linked with computer codes and displayed in an organized manner, such as alphabetically |
| Food Identification Catalogue | A food list with computer codes in the form of barcodes |
| Ingredient | A food that is a component of a food mixture, such as in a recipe |
| Leftovers | Some amount of food which was weighed-in, but not consumed |
| Plate | A plate or container for any food |
| Prompt | Require the user to respond to a query; the user may select options or provide numeric or textual responses via any input device, such as keyboard, mouse, voice recognition system or barcode reader, etc. |
| Resident Foodlist | The food list residing on the system of the invention |
| Record | Collect format and store data in data record in storage 4 (FIG. 1) |
| Scale | An electronic balance |
| Scraps | Inedible food portions such as bones, skins, seeks, corn cobs or cores, etc. |
| User | The person using the method and system of the present invention |
| Very Small Weight | A weight less than two grams |
| Weigh-In | The process by which a food to be eaten by the user is weighed, described, and recorded |
| Weigh-Out | The process by which the system of the Invention obtains a final food weight for all foods weighed-in by the user |
| Weight | The weight as recorded by an electronic balance and digitally reported, as well as the date and time the weight was recorded |
| Wrapper | An outer food covering composed of an inedible material such as paper or plastic |

I. PRESENTATION OF HARDWARE COMPONENTS

A schematic representation of the primary components required for a computerized dietary measurement system of the present invention is shown in FIG. 1. An input means 1 transmits alpha-numeric and digitized information to the control and logic system 2 which determines if the data is to be recorded in storage 4 or sent to the output/display means 3 for further user input. If the data is sent to the output/display means 3, it can be displayed exactly as inputted by the user so it can be displayed in a transformed format following calculations or data interpretation conducted by the control and logic system 2. Data records stored in the storage system 4 can be retrieved by the control and logic system 2 for calculations and/or knowledge gathering purposes. The system can be used by one or more users.

A preferred embodiment of the dietary measurement system is shown diagrammatically in FIG. 2. The system includes at least one computer or microprocessor 17, equipped with a system clock 11, control and logic system 2 (FIG. 1) and storage means 4 (FIG. 1). The computer 17 can be a portable computer which is coupled with an electronic balance 12, an input means 10 (such as a keyboard, mouse, voice recognition system), a visual output/display device 15 (such as a computer screen or CRT), an auditory display means 16, and optionally barcode reader input means 13, a modem 18, and a video image recording and storage input means 14. The computer 17 may also be coupled with a computer resource containing a food code administration database 19 for providing numeric computer codes associated with various foods. The electronic balance 12 communicates digital weight information to the control and logic system 2 (FIG. 1) located in computer 17 (FIG. 2). The control and logic system 2 (FIG. 2) then records the weight information, stores the data records in storage 4 (FIG. 1), and determines if further record clarification is needed from the user. If the latter is true, the control and logic system 2 (FIG. 2) prompts the user for further information through use of the visual output display means 15 and/or the auditory display means 16. The input means 10 allows the user to communicate with computer 17 by responding to prompts generated by the control and logic system 2 (FIG. 1) of computer 17. The system clock 11 provides the date and time stamp for every data record. The optional barcode reader input means 13 is an alternate means of inputting food code information. The optional video image recording and storage input means 14 records and stores video image data and video image control data for later digital transmission to computer 17, or to alternate computer system for storage and processing. The optional modem 18 is needed if data records must be transmitted via telephone lines to other computer(s) for processing, calculation, storage, and/or for consumption analysis.

II. RELATIONSHIP OF DATA COLLECTION TO THE CONSUMPTION ANALYSIS

Another preferred embodiment of the dietary measurement system of the present invention is schematically shown in FIG. 3. The system includes both a dietary data collection function and a consumption analysis function. However, the system of the present invention may include the data collection function only, and the computer 17 (FIG. 2) may have a modem for communication with other computer systems which have a consumption analysis function, as shown in FIG. 2. One or more users may use a single system of the invention to weigh and record their food intake. The system encompasses user services which include a pluralty of options and directives for correct measurements of different foods without need of changing a user's dietary habits. The initial weight of the food is measured on the electronic balance 12 (FIG. 2) using any one of the possible "Weigh Food In" options 30 selected from a secondary menu 52 (FIG. 4) by the user. The digitized weight is transmitted to computer 17

(FIG. 2), processed by its control and logic system 2 (FIG. 1) and stored in storage 4 (FIG. 1) as a data record 36. Associated with every data record is such information as time and date of the transaction, the "weigh food in" option 30 used for the transaction, food container weights associated with the particular weighed-in food, all user-entered food description information, and all user-entered textual comments concerning the transaction. Following food consumption, the user selects from the appropriate weigh food out option 32 from the secondary menu 52 (FIG. 4) to measure the weight of the food consumed. Such information as the weight of the uneaten food, the weight of any previously unweighed food container(s), the time and date stamp, and any user-entered textual comments concerning the transaction are processed by the control and logic system 2 (FIG. 1) and stored in storage 4 (FIG. 1) as a data record 36. After the weigh-out process has been completed for the food(s) eaten by the user, he/she selects a food coding option 34 from the main menu options 50 (FIG. 4) in order to specifically identify the food eaten. Food identification is accomplished by having the user choose the correct food description for each food consumed from the resident food list on computer 17. Optionally the barcode input means 13 (FIG. 2) can be used to input the correct computer code from a food identification catalogue and/or from the universal products codes displayed on packaged foods. The alpha-numeric computer code associated with each food description is stored in the data record 36 for standard food component calculations 40. These calculations can be conducted on the computer 17 or another host computer to which the data records 36 have been transmitted via modem 18 (FIG. 2). Standard food component calculations 40 calculate the amount of a nutrient or other food component(s) present in the food consumed by the user. This is accomplished by combining the gram weight of the food consumed by the user with the appropriate Food Component Data Bank(s) 38 to yield the amount of the nutrient(s) or other food component(s) present in the food consumed by the user. Linkage of the foods consumed by the user to the Food Component Data Bank(s) is accomplished through the use of alphanumeric food codes. The total consumption analysis 42 is calculated by totalling the amount of the food component(s) in all the foods consumed by a user over a specified time period, such as 24 hours, and is expressed in a variety of ways, such as total food component amount consumed per 24 hours, consumed per 1000 kilocalories, etc. The results of total consumption analysis 42 can be provided immediately to the user or stored for later use by the researcher, depending on the application of the invention.

III. TOP LEVEL USER INTERACTION

A schematic representation of the preferred options available to the user for interacting with computer 17 (FIG. 2) are shown in FIG. 4. Five options are available to the user at the main menu level 50. These include the weighing-in of food, the weighing-out of food, the selection of food codes for foods consumed, the recording of recipe information, and the entering of user-generated questions and/or comments regarding transactions. Selection of a main menu option 50 by the user, indicated through input means 10 (FIG. 2), provides the user access to secondary menu options 52 for the weigh-in and weigh-out of foods and for making a recipe. Choice of a secondary menu option 52 for the "Weigh-Food-In" and "Weigh Food Out" options is indicated by the user through input means 10 (FIG. 2), and provides access to the tertiary menu options 53 and finally to the routines described in FIGS. 5.A.1 through 5.C.5. The tertiary menu options 53 allow for flexibility in the eating habits of potential users while ensuring accurate data collection. Choice of a secondary menu option 52 for "Making a Recipe" routes the user to the routines in FIG. 5.B.1 and 5.B.2. Selection of the "Code Foods" or the "Enter Questions or Comments" options from the main menu 50 routes the user to the routines in FIG. 5.D.1 and FIG. 5.D.5, respectively.

IV. INDIVIDUAL INTAKE FOOD WEIGH-IN METHODS

IV(a) Food Weighing Method

FIGS. 5.A.1, 5.A.2, 5.A.3, 5.A.4, 5.A.5 and 5.A.6 depict flow diagrams for routines to assure that any food which is to be eaten by the user is recorded accurately. To arrive at the start point for any of these routines, the user selects the "Weigh Food In" option from the main menu options 50 (FIG. 4) and the "Weigh Food" option from the secondary menu options 52 (FIG. 4). The user is then prompted by the control and logic system 2 (FIG. 1) to place the food and any associated containers on the electronic balance 12 (FIG. 2) and to specify what is on the balance by selecting "Empty Plate", "Both Food and Plate", or "Food Only" from the tertiary menu options 53 (FIG. 4) using input means 10 (FIG. 2). If the user selects "Empty Plate" the control and logic system 2 (FIG. 1) directs the user to the "Empty Plate" process (FIG. 5.A.1). The plate is on the scale (block 100) so in block 102, the control and logic system 2 (FIG. 1) records the weight of the plate. Then, in block 104, the user describes the plate using input means 10 (FIG. 2) and the control and logic system 2 (FIG. 1) records this textual description. Next, in block 106, the control and logic system 2 (FIG. 1) forwards the user to procedures in block 120 (FIG. 5.A.3). At block 120 (FIG. 5.A.3), the control and logic system 2 (FIG. 1) checks the storage 4 (FIG. 1) and lists on display devices 15 and/or 16 (FIG. 2) the foods which to this point have been weighed-in and recorded. At this point, block 122, the user is given an opportunity to stop the weighing process. If the user chooses to stop the weigh-in routine, then the control and logic system 2 (FIG. 1) returns the user to the weigh-in secondary menu option 52 (FIG. 4) and outputs to display devices 15 and/or 16 (FIG. 2) a current list of foods weighed-in and recorded but not weighed-out. If at block 122 the user chooses to continue with the food weighing routine, then in block 124 the control and logic system 2 (FIG. 1) prompts the user to add a single food to the plate that is already on the electronic balance 12 (FIG. 2). In block 126 the control and logic system 2 (FIG. 1) records the combined weight of the food and plate and calculates the net weight of the food. In block 128 the control and logic system 2 (FIG. 1) prompts the user to enter, using input means 10 (FIG. 2), a textual description of the food which is then recorded by the control and logic system 2 (FIG. 1). At this point, the control and logic system 2 (FIG. 1) routes the user back to actions in block 120 (FIG. 5.A.3) in order for the user to continue weighing additional foods onto the same plate.

If the user chooses the "Both Food and Plate" selection (FIG. 5.A.2) from the tertiary menu options 53

(FIG. 4), then the control and logic system 2 (FIG. 1) displays directives (block 108) for the user to place a plate containing a single food on the electronic balance 12 (FIG. 2). Then, the control and logic system 2 (FIG. 1) records the combined weight of the plate and food (block 110) while in block 112 it tags the data record to show that the food was weighed-in with a plate. Next, in block 114 the user is prompted to enter a textual description of the plate weighed-in using in-put means 10 (FIG. 2), while the control and logic system 2 (FIG. 1), in block 116, records this information. In block 118, the control and logic system 2 (FIG. 1) routes the user to actions in block 120 (FIG. 5.A.3) in order for the user to continue weighing additional foods onto the same plate.

If the user chooses to weigh a food in a wrapper (FIG. 5.A.4), such as a bag of potato chips, then the user selects "Both Food and Plate" from the tertiary menu options 53 (FIG. 4). The control and logic system 2 (FIG. 1) then prompts the user to place the food contained in the wrapper on the electronic balance 12 (FIG. 2). In block 134, the control and logic system 2 (FIG. 1) records the combined weight of the food and wrapper while it tags the record to show that the food was weighed-in with a wrapper (block 136). In block 138, the control and logic system 2 (FIG. 1) prompts the user to record a textual description of the wrapper while the control and logic system 2 (FIG. 1) records the information. Next in block 140, the user is prompted to input a textual food description and the control and logic system 2 (FIG. 1) records the information. In block 142, the control and logic system 2 (FIG. 1) forwards the user to procedures in block 120 (FIG. 5.A.3) in order for the user to add additional foods to the food and wrapper.

If the user chooses to weigh a food packaged in a container (FIG. 5.A.5), such as a carton of yogurt, the user selects "Both Food and Plate" from the tertiary menu options 53 (FIG. 4). The Control and logic system 2 (FIG. 1) then prompts the user in block 144 to place the food and container on the electronic balance 12 (FIG. 2) and in block 146 records this weight. Meanwhile, the control and logic system 2 (FIG. 1) tags the record to indicate that the food was weighed with a container (block 148), prompts the user to enter a textual description of the container (block 150) and of the food (block 152), and then records this information. In block 154, the control and logic system 2 (FIG. 1) routes the user to the directives in block 120 (FIG. 5.A.3) in order to continue weighing additional foods onto or into the same container.

If a user chooses the "Food Only" selection (FIG. 5.A.6) then in block 156 the user places the single food without any associated container on the electronic balance 12 (FIG. 2), and the control and logic system 2 (FIG. 1) records the food weight (block 158). In block 160, the control and logic system 2 (FIG. 1) records in the data record that this food was not weighed with a container. Next, in block 162 the user is prompted to provide a textual description of the food using input means 10 (FIG. 2), and the control and logic system 2 (FIG. 2) records the information. In block 164 the user is returned by the control and logic system 2 (FIG. 2) to the weigh in secondary menu options 52 (FIG. 4). The control and logic system 2 (FIG. 2) then outputs to display devices 15 and/or 16 (FIG. 2) a listing of food that have been weighed in and recorded, but not weighed-out.

IV(b) DRINK WEIGHING METHODS

To weigh-in drinks, the user selects one of several approaches (FIG. 5.A.7 through 5.A.11). To arrive at the start point for any of these routines, the user selects the "Weigh Food In" option from the main menu options 50 (FIG. 4), the "Weigh Drinks" option from the secondary menu options 52 (FIG. 4), and the appropriate selection(s) from the tertiary menu options 53 (FIG. 4). At this latter level, the user is prompted by the control and logic system 2 (FIG. 1) to select, using input means 10 (FIG. 2), whether the drink is contained in a (1) bottle, can, or carton or (2) cup or glass.

If the drink is contained in a bottle, can or carton, then the control and logic system 2 (FIG. 1) routes the user to the procedures in FIG. 5.A.7. At block 166 the user places a drink packaged in a bottle, can, or carton on the electronic balance 12 (FIG. 2), and the control and logic system 2 (FIG. 1) records the combined weight (block 168). In block 170, the control and logic system 2 (FIG. 1) tags the data record to indicate that the bottle, can, or carton with which the drink was weighed will need to be weighed later, while in block 172 it records that the container was a bottle, can, or carton. Next, in block 174 the control and logic system 2 (FIG. 1) prompts the user to enter a textual drink description and then records this information into the data record. The user is then routed back to the weigh-in secondary options menu 52 (FIG. 4) and the control and logic system 2 (FIG. 1) outputs to the display devices 15 and/or 16 a listing of all foods that have been weighed in but not weighed.

If the drink will be contained in a cup, or a glass, the user is prompted by the control and logic system 2 (FIG. 1) to place the cup on the electronic balance 12 (FIG. 2) and to select, using input means 10, whether the cup or glass is empty, or contains the drink, or has ice in it. If the cup is empty (FIG. 5.A.8) the user starts with the weighing routine at block 178. In block 180 the control and logic system 2 (FIG. 1) records the weight of the empty cup from the electronic balance 12 (FIG. 2). Next, the control and logic system 2 (FIG. 1) prompts the user for a textual description of the empty cup. In block 182, after recording this description, the control and logic system 2 (FIG. 1) advances the user (block 184) to the routine for adding drinks to cups (FIG. 5.A.11).

If the drink is already in the cup (FIG. 5.A.9) the user begins the weighing routine by selecting from the tertiary menu options 53 (FIG. 4) that a cup containing a drink (block 186) has been placed on the electronic balance 12 (FIG. 2). The control and logic system 2 (FIG. 1) records this combined weight in block 188 and tags the data record indicating that the drink was weighed with a cup that needs to be weighed and recorded later (block 190). In block 192, the control and logic system 2 (FIG. 1) prompts the user for a textual description of the cup which is then recorded by the control and logic system 2 (FIG. 1). Next, in block 194 the user is prompted for a description of the drink and the description is recorded. Then the control and logic system 2 (FIG. 1) forwards the user (block 196) to the routine for adding additional drinks to the cup (FIG. 5.A.11).

If the cup contains ice but no drink (FIG. 5.A.10), then the user is prompted in block 198 to place the cup with ice on the electronic balance 12 (FIG. 2). At block 200, the control and logic system 2 (FIG. 1) records the combined weight of the cup with ice and in block 202 tags the data record to indicate that the cup has not been weighed and will need to be weighed later (block 202). In block 204, the control and logic system 2 (FIG. 1) prompts the user for the textual cup description and records this information into the data record. Next, in block 206 the control and logic system 2 (FIG. 1) records into the data record that ice was contained in the cup, and then routes the user (block 208) to the routine for adding drinks to cups (FIG. 5.A.11).

If additional drinks or other foods are to be added to the cup (FIG. 5.A.11), the control and logic system 2 (FIG. 1) searches storage 4 (FIG. 1) and displays on display devices 15 and/or 16 a list of drinks and foods which have already been weighed into this cup, block 210. If the user chooses not to add additional drinks or foods to the cup, he/she stops the weighing routine (block 212), and is then routed (block 214) to the weigh-in secondary menu options 52 (FIG. 4) by the control and logic system 2 (FIG. 1) which also outputs to the display devices 15 and/or 16 a listing of all foods that have been weighed in but not weighed out. If the user chooses in block 212 to continue with the weighing procedure, then directives are provided to the user in block 216 to add a single drink or food to the cup on the electronic balance 12 (FIG. 2), in block 218, the control and logic system 2 (FIG. 1) records the total weight and then calculates and records the net weight of the last drink/food added to the cup. In block 220 the control and logic system 2 (FIG. 1) prompts the user for a textual description of the last food or drink added to the cup and records the information. The user is then routed to block 210 by the control and logic system 2 (FIG. 1) in order to continue the weighing of additional drinks or food to the cup or to stop the weighing process.

IV(c) SECOND HELPING OF FOOD/DRINK

FIG. 5.A.12 is a schematic flow diagram of the procedure for weighing in second helpings of already recorded foods. The routine provides the flexibility to eat second helpings while it assures that such food weight(s) are accurately weighed and recorded. When a user chooses the second helpings secondary menu options 52 (FIG. 4), the routine begins at block 222 with the control and logic system 2 (FIG. 1) checking storage 4 (FIG. 1) and outputting to display devices 15 and/or 16 (FIG. 2) a list of foods which have been weighed-in but not yet weighed out. Then, in block 224, the user selects the food for a second helping from the displayed list. In block 226, the control and logic system 2 (FIG. 1) searches the data record to determine if the first helping was weighed in a bottle, can, or carton. If not, then in block 228 the control and logic system 2 (FIG. 1) checks the data record to see if the selected food was previously weighed without a container. If yes, then in block 230, the control and logic system 2 (FIG. 1) prompts the user to place the food on the electronic balance 12 (FIG. 2). Next, in block 232 the control and logic system 2 (FIG. 1) records the weight of the food, automatically enters the food description, and tags the record as a second helping (block 234). Then in block 258, the control and logic system 2 (FIG. 1) returns the user to the secondary weigh-in menu options 52 (FIG. 4) and outputs to display device 15 and/or 16 the current list of foods weighed-in but not yet weighed-out.

If at block 226, the control and logic system 2 (FIG. 1) determines that the first weighing of this food was with a bottle, can, or carton, then it proceeds to block 236 and prompts the user for information on whether the second helping is also in a bottle, can, or carton. If the response is yes, then the control and logic system 2 (FIG. 1) directs the user to place the food in the bottle, can, or carton on the electronic balance 12 (FIG. 1), block 248. Then, in block 250, the control and logic system 2 (FIG. 1) records the combined bottle and food weight into the data record while, in block 252, it tags the data record to indicate that the bottle must be weighed later. Next, in block 254, the control and logic system 2 (FIG. 1) automatically records the description "bottle, can, or carton" for the container description in the data record, and in block 256 flags the food as a second helping. Then, in block 258, the control and logic system 2 (FIG. 1) routes the user back to the secondary weigh-in menu options 52 (FIG. 4) and outputs to display devices 15 and/or 16 (FIG. 2) current list of foods weighed-in but not yet weighed-out.

If at block 236 the user indicates that the second helping is not a "bottle, can, or carton," then in block 238 the control and logic system 2 (FIG. 1) prompts the user for a plate or cup description which is subsequently recorded. In block 240, the control and logic system 2 (FIG. 1) prompts the user to place the plate or cup on the electronic balance 12 (FIG. 2) while in block 242 it records this container weight. Next, in block 244, the control and logic system 2 (FIG. 1) instructs the user to add the second helping of food to the plate or cup located on the electronic balance 12 (FIG. 2). In block 246, the control and logic system 2 (FIG. 1) records the combined food and container weight, computes the net weight of the second helping of food, and records the combined weight and the net weight. Next, the control and logic system 2 (FIG. 1) flags the food as a second helping in the data record, block 234. The user is then routed back to the secondary weigh in menu options 52 (FIG. 4) by the control and logic system 2 (FIG. 1), and the curent list of foods weighed-in but not yet weighed-out is outputted to display devices 15 and/or (FIG. 2 by the control and logic system 2 (FIG. 1).

V. BULK FOOD WEIGH-IN METHODS

V(a) Ingredients

FIG. 5.B.1 depicts a flow diagram for the recipe ingredient weighing routine for bulk foods. This routine assures that each food in a recipe is weighed, identified, and recorded accurately. To arrive at the start point for this routine, the user selects, using input means 10, the "Make a Recipe" option from the main menu options 50 (FIG. 4) and "Ingredient Recording" option from the secondary menu options 52 (FIG. 4). The user is then prompted by the control and logic system 2 (FIG. 1) to enter the name of the recipe for which the ingredients are being recorded (block 260). Next, the control and logic system 2 (FIG. 1) prompts the user to enter descriptions of the ingredients in the recipe (block 262), if needed, displays the list of ingredients for the user (block 264), and prompts the user to select a menu option from block 266, for the next routine to be taken.

If at block 266, the user chooses "Edit Ingredient List" then the control and logic system 2 (FIG. 1) provides directives for the user to change, delete, or add the ingredient name(s) to the list and displays for the user the current list of ingredients. If the user chooses the "Weigh-in Ingredients" routine at block 266, then the control and logic system 2 (FIG. 1) routes the user to the standard "Weigh Food In" options within the secondary menu options 52(FIG. 4). If at block 266 the user chooses the "Weigh-out Leftover Ingredients" routine, then the control and logic system 2 (FIG. 1) routes the user to the standard Weigh Food Out Options (FIG. 5.C.1 through 5.C.5) within the secondary menu options 52 (FIG. 4). If the user chooses to assign a food code to the weighed-in ingredient descriptions then he/she is routed by the control and logic system 2 (FIG. 1) to the standard "Code Food" routine (FIG. 5.D.1). After the user completes the weigh-in, weigh-out, or coding of an ingredient, the user is then returned to block 600. When the user chooses to weigh empty cooking/mixing containers, the control and logic system 2 (FIG. 1) prompts the user to place the empty container on the electronic balance 12 (FIG. 2) (block 268), records the weight into storage 4 (FIG. 1) at block 270, and returns the user to the ingredients and menu options (block 264). At block 266, if the user chooses the "Enter Comments" routine, then he/she is routed by the control and logic system 2 (FIG. 1) to the "Enter Questions or Comments" routine (FIG. 5.D.5). When the "Exit" option is selected by the user, the control and logic system 2(FIG. 1) routes the user back to main menu options 50 (FIG. 4).

V(b) FINAL RECIPE WEIGHTS

FIG. 5.B.2 depicts a flow diagram for measuring and recording the final weight of the total recipe mixture and for recording the cooking method(s) used. To arrive at the start point for this routine, the user selects the "Make a Recipe" option from the main menu 50 (FIG. 4) and then the "Final Recipe Weights" option from the secondary menu options 52 (FIG. 4). Upon arrival at the start point block 280, the control and logic system 2 (FIG. 1) displays the recipes in progress. If the user interrupts the routine (block 282) then the control and logic system 2 (FIG. 1) routes the user back to main menu options 50 (FIG. 4). If the user makes no Interruptions, the control and logic system 2 (FIG. 1) prompts the user to select a recipe to process (block 284). Next, the user is prompted to select the cooking method(s) used from a display list (block 285), and then to place on the electronic balance 12 (FIG. 2) the total recipe mixture in its cooking/mixing container. Next, the control and logic system 2 (FIG. 1) computes the net weight of the recipe mixture (block 288), records this weight (block 288), removes the recipe from the display list (block 290), and displays for the user an updated list of recipes in progress (block 250).

VI. INDIVIDUAL INTAKE FOOD WEIGH-OUT METHODS

VI(a) Single Food Weigh-Out

FIG. 5.C.1 depicts a flow diagram of a single food weigh-out procedure. The routine assures that any food which has been weighed-in and recorded (FIG. 5.A.1 through FIG. 5.A.12) and which has not been merged with another food during eating, meaning it can be separated from other foods, will have a properly computed and recorded consumption weight.

At block 302, the control and logic system 2 (FIG. 1) displays from storage 4 (FIG. 1) a list of foods which have been weighed-in. Then in block 304, the user determines which food to weigh-out and enters the selection with input means 10 (FIG. 2). In block 306, control and logic system 2 (FIG. 1) retrieves all descriptive information regarding the food to be weighed out from storage 4 (FIG. 1) and this information is transferred to the display devices 15 and/or 16 (FIG. 2).

In block 308, the user is prompted by display devices 15 and/or 16 (FIG. 2) to indicate whether any of the food has been eaten. If the food has not been eaten, the user confirms in block 310 using input means 10 (FIG. 2) and the data record for this food is tagged as "Food Not Eaten" (block 312) by the control and logic system 2 (FIG. 1) and returned to storage 4 (FIG. 1). The user is then returned to the display of foods which need to be weighed out (block 302). If there are no foods remaining to be weighed out or if the user chooses to stop the weigh-out process, then in block 300 the user confirms, and the control and logic system 2 (FIG. 1) returns the user to the secondary weigh-out menu options 52 (FIG. 4). If the user rejects the confirmation in block 300, the Logic System 2 (FIG. 1) routes the user back to block 304. Additionally, if the user rejects the confirmations in block 310, the control and logic system 2 (FIG. 1) routes the user back to block 306.

If in block 308 the user indicates that some of the food has been eaten, then in block 314 the control and logic system 2 (FIG. 1) prompts the user for information on leftovers and/or scraps. If the user confirms that the food has no leftovers or scraps (block 316), then in block 318 the control and logic system 2 (FIG. 1) checks the data record to determine if any unweighed plates, cups, or bottles were associated with the food. If no, then block 320, the data record is tagged as "complete" by the control and logic system 2 (FIG. 1) and is returned to storage 4 (FIG. 1). The user is then returned to the secondary weigh-out menu options 52 (FIG. 4).

If in block 318 the control and logic system 2 (FIG. 1) finds that there is a plate, cup, or bottle which needs to be weighed, then in block 322 the description of the plate, cup, or bottle with its time and date stamp is shown on the display devices 15 and/or 16 (FIG. 2). In block 324, the user is prompted to choose whether the plate, cup, or bottle should be weighed now or at a later time. If the decision is to weigh the container at a later time, then in block 326 the control and logic system 2 (FIG. 1) tags this message on the data record and files the record to storage 4 (FIG. 1). The control and logic system 2 (FIG. 1) then returns the user to the secondary weigh-out menu options 52 (FIG. 4). If the decision in block 324 is to weigh the container now, then the control and logic system 2 (FIG. 1) displays instructions using the display devices 15 and/or 16 (FIG. 2). In block 328, the user places the empty plate, cup, or bottle on the electronic balance 12 (FIG. 2) while in block 330, the control and logic system 2 (FIG. 1) records the weight of the plate, cup, or bottle into the record. Then, in block 332 the control and logic system 2 (FIG. 1) calculates the net weight of the food eaten while in block 334 the record is tagged as "complete" and sent by the control and logic system 2 (FIG. 1) to storage 4 (FIG. 1). The control and logic system 2 (FIG. 1) then returns the user to the secondary weigh-out menu options 52 (FIG. 4).

If the user's response in block 314 was that there are leftovers and/or scraps for the food, then in block 336, the control and logic system 2 (FIG. 1) checks storage 4 (FIG. 2) to determine if the selected food was originally weighed-in as "food only" (FIG. 5.A.6). If the answer is yes, instructions are sent by the control and logic system 2 (FIG. 1) to display devices 15 and/or 16 (FIG. 2) for the user to place (block 338) the leftover and/or scraps with or without a container on the electronic balance 12 (FIG. 2). Next, in block 340, the control and logic system 2 (FIG. 1) records the total weight of the food or scraps and any container. Then, in block 342, the control and logic system 2 (FIG. 1) prompts the user as to whether the food was weighed on a plate or in a cup. If the answer is no, then the control and logic system 2 (FIG. 1) proceeds to block 348 and calculates and records the net weight of the food eaten. In block 350, the data record is tagged as complete and the control and logic system 2 (FIG. 1) returns the user to the secondary weigh-out menu options 52 (FIG. 4). If in block 342 the control and logic system 2 (FIG. 1) finds that the leftover was weighed on a plate or in a cup then, in block 344 the control and logic system 2 (FIG. 1) forwards instructions/prompts for the user to display devices 15 and/or 16 (FIG. 2). The user removes leftovers or scraps from the plate or cup and returns the plate or cup to the electronic balance 12 (FIG. 2), in block 346, the control and logic system 2 (FIG. 1) records the weight of the empty plate or cup, calculates and records the total and net weight of food eaten (block 348), tags the data record as complete (block 350) and returns the user to secondary weigh-out menu options 52 (FIG. 4).

If in block 336 the control and logic system 2 (FIG. 1) finds that the food was not originally weighed as "food only", then in block 352, the control and logic system 2 (FIG. 1) checks if the food was originally weighed with a bottle, can or carton. If no, then in block 354 prompts/instructions are displayed on display devices 15 and/or 16 (FIG. 2) and the user places the leftover and container on electronic balance 12 (FIG. 2). In block 356, the control and logic system 2 (FIG. 1) records the total weight of leftover and container into the data record, and the actions in blocks 344 to 350 are performed. If in block 352 the food was originally weighed with a bottle, can or carton, then the control and logic system 2 (FIG. 1) in block 358 searches the data record to determine if the leftover food is currently in a cup or still in the original bottle, can, or carton. If the leftover has been transferred to a cup then the control and logic system 2 (FIG. 1) sends directives to display devices 15 and/or 16 (FIG. 2). In block 360, the user follows the directives and places the leftover and cup on electronic balance 12 (FIG. 2). In block 362 the control and logic system 2 (FIG. 1) records the total weight and in block 364 directs the user to remove the leftover from the cup and then to return the cup to the electronic balance 12 (FIG. 2). In block 366, the control and logic system 2 (FIG. 1) records the weight of the empty cup. Next, in block 368 the control and logic system 2 (FIG. 1) directs the user to place on the electronic balance 12 (FIG. 2) the original bottle and any leftovers which may still be in it and then advances the user to the action in 348 and 350. If in block 358 the leftover food is still in the original bottle, then the control and logic system 2 (FIG. 1) advances the user to the actions in blocks 368, 348, and 350.

VI(b) MERGED LEFTOVERS WEIGH-OUT

FIG. 5.C.2 depicts a flow diagram of the merged leftovers weigh-out routine. The routine assures that any food which has been weighed-in and recorded (FIGS. 5.A.1 through 5.A. 12), and which has been merged together with another food during eating, meaning that one food can no longer be separated from the other, will have a properly computed and recorded consumption weight.

In block 400, the control and logic system 2 (FIG. 1) displays from storage 4 (FIG. 1) a list of foods that have been weighed-in and recorded together with those foods recently weighed out. Then in block 402, the user indicates which foods are merged together. In block 404, the control and logic system 2 (FIG. 1) lists the selected foods and requests a user confirmation. If the merged foods listed are incorrect, then the control and logic system 2 (FIG. 1) routes the user back to block 402. If the user acknowledges that the foods indicated are merged, the control and logic system 2 (FIG. 1) displays directives on the display devices 15 and/or 16. In block 406, the user places the merged leftovers and plate or cup on the electronic balance 12 (FIG. 2) and the control and logic system 2 (FIG. 1) records the total weight (block 408). in Block 410, the user is directed to remove the merged leftovers from the plate or cup and to return the container to the electronic balance 12 (FIG. 2). The empty plate/cup weight is recorded by the control and logic system 2 (FIG. 1) in block 412. Then, in block 414, the control and logic system questions the user as to how much of each food has been eaten using pre-established quantity criteria. In block 416, the control and logic system computes from the user-supplied information the amount of each food eaten, while in block 418 it records the adjustments and net weight of each food consumed. Then, in block 420, for each food that the user indicated as a merged leftover, the control and logic system 2 (FIG. 1) checks the data record to assure that there are no unweighed plates, cups, or bottles which still need to be weighed. If there are such missing weights then the control and logic system 2 (FIG. 1) leads the user to block 352 on FIG. 5.C.1.c. If there are no missing weights for plates, cups, or bottles, then the control and logic system 2 (FIG. 1) tags the data record as complete and files the record in storage 4 (FIG. 1).

VI(c) UNWEIGHED PLATES, CUPS AND BOTTLES WEIGH-OUT

FIG. 5.C.3 depicts a flow diagram of the process for obtaining weights of unweighed plates, cups, and bottles. The routine assures that a data record contains no missing weights for plates, cups, and bottles for any foods recorded during the weigh-in and weigh-out procedures (FIG. 4), and therefore, that food consumption weights for an individual are accurate.

At block 430, the control and logic system 2 (FIG. 1) displays from storage 4 (FIG. 1) a list of containers which lack weights. In block 432, if the user does not want to weigh the listed containers at this time, or if there are no unweighed containers, then the user is returned to the weigh-out secondary menu options 52 (FIG. 4) by the control and logic system 2 (FIG. 1). If the user elects to weigh the containers, then in block 436, the user chooses which container to weigh out. In block 438, the control and logic system 2 (FIG. 1) prompts the user to confirm the selection. After a confirmation is received, in block 440, the control and logic system 2 (FIG. 1) directs the user to place the empty container on the electronic balance 12 (FIG. 2) and records its weight in block 442. In block 444, the control and logic system 2 (FIG. 1) computes and records the net weight of the food associated with this container, marks the date record as complete (block 446)

and returns (block 448) the user to the secondary weigh-out menu option 52 (FIG. 4).

VI(d) SPILLS WEIGH-OUT

FIG. 5.C.4 depicts the flow diagram of the spilled food routine. This routine assures that any food which has been weighed in and recorded (FIG. 5.A.1 through 5.A.12), but is spilled before it is weighed-out, will have a properly computed and recorded consumption weight.

At block 460, the control and logic system 2 (FIG. 1) sends directives to display device(s) 15 and/or 16 (FIG. 2) instructing the user to first clean up the spill. Next, the control and logic system 2 (FIG. 1) prompts the user as to whether any of the spilled food was consumed prior to spilling. If none of the food was eaten, then in block 464, the control and logic system 2 (FIG. 1) instructs the user to return to the "Weigh Food Out" secondary menu options 52 (FIG. 4) and to weigh-out the food using the procedures in block 302 through 312 of FIG. 5.C.1. In block 466, if the user had eaten some food prior to spilling, the control and logic system 2 (FIG. 1) provides directives for the user to place the clean up materials containing the spilled food(s) on the electronic balance 12 (FIG. 2). Then the control and logic system 2 (FIG. 1) records their combined weight (block 468). In block 470, the control and logic system 2 (FIG. 1) displays a list of weighed-in and recently weighed-out foods using display devices(s) 15 and/or 16 (FIG. 2). Next, in block 472, the user selects the name(s) of the foods which was (were) spilled. After receiving a confirmation in block 474 from the user, the control and logic system 2 (FIG. 1) prompts the user for the estimated amount of each food spilled using pre-established quantity criteria (block 476). In block 478, the user is instructed by the control and logic system 2 (FIG. 1) to remove the spilled food from the cleaning materials and to return the cleaning materials to the electronic balance 12 (FIG. 2). In block 480, the control and logic system 2 (FIG. 1) records the weight of the cleaning materials. Then, in block 482, the control and logic system 2 (FIG. 1) computes the weight of the food(s) consumed before the spill, and in block 484 it records the weight adjustments and the weight of food eaten. Next, the control and logic system 2 (FIG. 1) provides the user with an opportunity to record additional textual comments about the spilled food (block 496) and these are recorded. In block 488, the control and logic system 2 (FIG. 1) returns the user to the secondary weigh-out menu options 52 (FIG. 4).

VI(e) FORGOTTEN ITEMS WEIGH-OUT

FIG. 5.C.5 depicts a flow diagram for weighing, describing and recording foods, scraps, and containers that were missed during the weigh-out process. The routine assures that any food which has been both weighed-in and weighed-out will have an accurately calculated weight.

At block 496, the control and logic system 2 (FIG. 1) displays a list of foods recently weighed-out using display devices 15 and/or 16 (FIG. 2). When the user selects the name of the food to process (block 498), the control and logic system 2 directs (block 500) the user to place the forgotten item on the electronic balance 12 (FIG. 2), records the weight (block 502), and then prompts the user for a textual description of the forgotten item (block 504), which is then recorded. In block 505, the control and logic system 2 (FIG. 1) prompts the user to determine if the forgotten item is a container. If not, the control and logic system 2 (FIG. 1) prompts the user in block 506 to determine if the forgotten food or scrap was weighed with a container in block 502. If yes, the user is given directives by the control and logic system 2 (FIG. 1) to remove the food or scrap from the container (block 507) and to place the container on the electronic balance 12 (FIG. 2) in block 508. The empty container weight is then recorded by the control and logic system 2 (FIG. 1) in block 510, and the user is prompted for additional text comments concerning the forgotten food or scrap (block 512). The control and logic system 2 (FIG. 1) then routes the user to the "weigh food out" secondary menu options 52 (FIG. 4) in block 514.

If in block 505 the user indicates that the forgotten item is a container, the control and logic system 2 (FIG. 1) routes the user to the actions in block 512 and 514. If in block 506 the user indicates that the forgotten item was not weighed with a container in block 502, then the user is routed by the control and logic system 2 (FIG. 1) to the actions in blocks 512 and 514.

VII. SPECIAL DATA COLLECTION METHOD

VII(a) FOOD CODING METHODS

For every food weighed-in, the control and logic system 2 (FIG. 1) obtains from the user a textual description of the food or a food code through a barcode reader. When using the barcode reader, the user will utilize a food indentification catalogue to find a food description of the food being eaten and its associated barcode. In the preferred embodiment, the system is provided with at least one resident food list 804 (FIG. 5.D.3) which has food descriptions and associated computer codes. The food list may include names of food groups and names of food species under each food group. The food list can further include a food description for each food. The food descriptions in the database may include the important features of each food, such as species, color and appearance, processing method(s), cooking method(s), fortification(s), etc. The computer 17 of the system is programmed in such a way that the food description from the user, which may be the name of a food or words related to the features of the food, is used as key words to search the food in the database. When convenient, the user specifically identifies all foods eaten by using the food coding methods routine (FIG. 5.D.1). This routine (FIG. 5.D.1) assures that each food description selected for coding will have a properly recorded numeric computer code that can be used to link the food description to the appropriate Food Component Data Bank(s) 38 (FIG.3).

When the user chooses the "Code Foods" option from the main menu options 50 (FIG. 4), the control and logic system 2 (FIG. 1) displays for the user a list of uncoded food descriptions (block 600). If the user interrupts the coding process (block 602), then the control and logic system 2 (FIG. 1) routes the user back to the main menu options 50 (FIG. 4). When no interruptions occur, the user is prompted by the control and logic system 2 (FIG. 1) to select a food for coding or to allow the computer 17 to conduct an automatic food selection process (block 604). Next, the control and logic system 2 (FIG. 1) utilizes the food description generated by the user during the weigh-in process to search for a match between the user's food description and the food descriptions contained within the resident food list 804

(FIG. 5.D.3). The control and logic system 2 (FIG. 1) then sets the search index (block 606) and displays a section of the resident food list 804 (FIG. 5.D.3) with the selected food description having the closest match highlighted (block 608). At this point the control and logic system 2 (FIG. 1) also displays to the user a list of menu options. These options include selecting the highlighted food, searching further for a better match, recording that the food is not contained within the resident food list 804 (FIG. 5.D.3), or exiting the code food process (block 610). When the user selects either the highlighted food description or "Can't Find Food" options, the control and logic system 2 (FIG. 1) records the computer code from the resident food list 804 (FIG. 5.D.3) (block 612), and routes the user back to block 600 to continue the food coding process or returns the user to the main menu options 50 (FIG. 4) if all foods have been coded.

If at block 610, the user chooses to use a second or third word from his/her text food description to search for a better food description match, then the control and logic system 2 (FIG. 1) searches the resident food list, sets the search index (block 606), and displays the section of the food list with a new food highlighted (block 608). At block 610, the user also has a choice of entering a new textual food description with which the control and logic system 2 (FIG. 1) can search the resident food list 804 (FIG. 5.D.3) for a food description match (block 606). Or if the user wishes, he/she can use input means 10 (FIG. 2) to move the highlighter up and down through the resident food list 804 (FIG. 5.D.3) in order to choose the most appropriate match. When the control and logic system 2 (FIG. 1) and the user can not find a close match on the resident food list 804 (FIG. 5.D.3) for the user's text food description, then the user selects the "Can't Find" code option and the control and logic system 2 (FIG. 1) records into the data record that a code was not found. Then, the control and logic system 2 routes the user back to 600 to continue the food coding process. Another option for the user is "Code Food Later". When a user chooses this option, the control and logic system 2 (FIG. 1) routes the user back to the main menu option 50 (FIG. 4).

VII(b) HANDLING VERY SMALL WEIGHTS (FIG. 5.D.2)

FIG. 5.D.2 depicts a flow diagram of how the present invention handles a very small weight change. The routine assures that the control and logic system verifies and records any weight changes which are small. This procedure is followed whenever a food, plate, cup, bottle, or wrapper is added to the electronic balance 12 (FIG. 2). The routine begins with the control and logic system 2 (FIG. 1) obtaining from the electronic balance 12 (FIG. 2) the weight of an item recently placed on the electronic balance 12 (FIG. 2) (block 700). Next, the control and logic system 2 (FIG. 1) checks storage 4 (FIG. 2) for information as to whether the weight reported by the electronic balance 12 (FIG. 2) is different from the weight of the last reading (block 702). If the weight is not different, then the control and logic system 2 (FIG. 1) notifies the user that no weight change has occurred (block 704) and prompts him/her to reweigh the food (block 706). If the user wishes to reweigh the food then the control and logic system 2 (FIG. 1) routes him/her back to block 700. However, if the user prefers to not reweigh the food, then he/she will be routed to block 708 where the control and logic system 2 (FIG. 1) proceeds with more weight checks.

If at block 702 the control and logic system 2 (FIG. 1) finds a weight change since the last reading, then it checks to see if the weight change is zero or slightly negative (block 708). When the weight change is zero or slightly negative the control and logic system 2 (FIG. 1) questions the user as to whether any foods have been placed on the electronic balance 12 (FIG. 2). If the user did not place any food or drinks on the electronic balance 12 (FIG. 2), then the control and logic system 2 (FIG. 1) routes the user back to block 700 to being the weighing procedures again. If at block 710, the user indicates that an item was placed on the electronic balance 12 (FIG. 2), then the control and logic system 2 (FIG. 1) checks to see if the weight change is less than two grams (block 712). If the net weight is not less than two grams, then in block 722 the control and logis system 2 (FIG. 1) will record this net weight into the data record and return the user back to his/her weighing routine.

When a net weight is less than two grams, the control and logic system 2 (FIG. 1) will prompt the user for information as to whether the item on the electronic balance 12 (FIG. 1) is a small item like a wrapper or a small quantity of food (block 714). If the response is yes, then the control and logic system 2 (FIG. 1) checks to see if the net weight is less than one gram (block 718). If yes, then the conrol and logic system 2 (FIG. 1) tags the data record for low net weight (block 720) and returns the user to proceed with the weighing routine (block 722). If at block 714 the user indicates that the item on the electronic balance 12 (FIG. 2) is not a small weight item such as a wrapper, then the control and logic system 2 (FIG. 1) prompts the user to reset the electronic balance 12 (FIG. 2) to zero (block 716) and to reweigh the item (block 700).

VII(c) ENABLING MULTIPLE SOURCES FOR SCIENTIFIC FOOD DATA

FIG. 5.D.3. depicts how the present invention enables multiple Food Component Data Banks (FCDB) to be used to calculate the amount of nutrient(s) or other food component(s) present in the food(s) consumed by the user. This modular approach to utilizing food composition data enables the invention to calculate an individual's dietary consumption of any component present in foods and for which food composition data is available, such as energy, nutrients, cholesterol, food additives, toxic elements, and pesticide residues. FIG. 5.D.3 shows how computer codes and descriptions in the resident food list 804 on computer 17 (FIG. 2) are linked to the food codes and descriptions in the Food Component Data Bank(s) 810. Each food record in a Food Component Data Bank (block 810) contains, in specified fields, a food code, a food description, and selected food composition information. The Food Administration Data Bases(s) in block 812 utilizes FCDB food codes and FCDB food descriptions in order to create a custom-designed food list with unique computer codes and with food descriptions comprehensible to the average lay person. It is this custom-designed food list which resides on computer 17 (FIG. 2), and constitutes the resident food list in block 804. When only one FCDB is utilized, the computer code may be the FCDB food code and the food description may be the FCDB food description. Using the food coding methods (FIG. 5.D.1), the user utilizes the resident food list 804 to identify foods eaten 800 and 802. In order for total consumption analysis to be performed, each food data record must contain a computer code and the weight of the food eaten (block 806). When the data records are analyzed (block 807), the control and logic system 2 (FIG. 1) uses the computer code in each data record for linkage to a FCDB food code for each FCDB to be utilized (block 810) in order to compute the nutrient/food component values for each food recorded (block 808), and to calculate the total consumption information for each user (block 814). The Food Component Data Bank(s) may reside on the measurement system of the invention or on remote computer resources.

VII(d) ENABLING ACCURATE USE BY GROUPS WITH DIFFERENT READING LEVELS, LANGUAGES, TECHNICAL SKILLS AND SOCIO-ECONOMIC BACKGROUNDS

By enabling the system's interaction with the user to be adapted without reprogramming, the invention has the capability for use by individuals with comprehension differences attendant to differing reading levels, languages, technical skills, ethnic and regional origins and socio-economic levels. All visual and auditory displays and messages, as well as standard system responses are contained in text files which can be easily modified to reflect the skills of the user. These text files are contained within the screen/messages display data base (block 852) and the keyboard response data base (block 860). The screen/messages display data base 852 contains the following components: (1) the 'text locator number' 853 which is the screen number; (2) the 'text format control' 854 which is information, such as row and column numbers, needed to correctly place prompts/messages/directives on the visual display output means 15 (FIG. 2), (3) the 'text to be displayed' 855 is the screen information to be outputted to the user via display means 15 and/or 16 (FIG. 2), (4) the 'beep control' 856 is the information which specifies in which of the invention's routines/processes the beep/tone mechanism should be enacted, the number of beeps or the length of time to sound the tone, and the pitch of the beep or tone, (5) the 'synthesized/digitized speech control, 857 is the information needed to control speech output (both synthesized and digitized speech) via auditory display means 16 (FIG. 2) that specifies in which of the invention's routines/processes speech should be outputted to the user, what should be said, the pitch of the voice to be used, the rapidity of the speech, and in the case of synthesized speech, the phonetic equivalent of the text message to be outputted, and (6) the 'text locators or other text to also be displayed' 858 contains the screen numbers for a multiple part text message. Modifications to these databases 852 and 860 change the visual/auditory prompts, messages, and standard system responses throughout the applications software block 850, thus enabling use of the applications software by varied users without the need for reprogramming.

VII (e) ERROR DETECTION METHODS IN THE WEIGHING PROCESS

During the individual and bulk food weigh-in and weigh-out processes, the magnitude of earlier data record weights is compared to current weights being taken for the purpose of error detection. A small weight change is enacted whenever a weight change of less than 2 grams occurs in any of the weigh-in or weigh-out routines. This process is fully described in FIG. 5.D.2. When additional food or drink is added to a plate or cup, a check is used to ensure weight increases. During the weighing of leftovers, a check for "ever-decreasing" weights is enacted to ensure that the user removes the leftover(s) from the container, and an additional check is used to ensure that the leftover food weight does not exceed the weight of the original weigh-in food. These same checks are also used during the spill and merged leftover routines. During the unweighed plates, cups and bottles routines, checks are used to ensure that the container does not exceed the original food and container weight recorded during weigh-in, and that the container weight does not exceed the original weighed-in food and container weight minus the leftover food weight. During second helpings routine, the second helping weights are added to the original food weights for the purposes of error detection.

VII(f). COLLECTION OF USER COMMENTS

The invention provides the user numerous opportunities to enter, using input means 10 (FIG. 2), textual information regarding actions taken, problems incurred, or even questions and general comments. In addition, this routine can be used to record descriptions and estimated quantities for foods eaten without using other routines of the invention. FIG. 5.D.5 depicts the routine used to collect free-form textual information from the user. In block 900, the control and logic system 2 (FIG. 1) prompts the user to enter any number of lines of text. After a line of text is collected, in block 902, the control and logic system 2 (FIG. 1) prompts the user to determine if the comments are complete (block 904). If the answer is no, then in block 908 the control and logic system 2 (FIG. 1) records one line of text to a data record while determining (block 910) if text line exceeds the maximum allowable length. If the answer is no, the user is returned to block 902 to continue adding additional lines of text. If the answer is yes, the control and logic system 2 (FIG. 1) wraps that portion of the text exceeding the maximum line length to the next line (block 912) and then returns the user to block 902 to continue adding additional lines of comments. If in block 904 the user indicates that the comments are complete, then the user is returned to the actions in weigh-in, weigh-out, food coding, or recipe procedures, depending on the current location of the user.

VII(g). FOOD INTAKE DATA RECORD

The following list shows an example of the contents of the basic food intake data record which can be collected by the system of the invention (but not limited to these).

DATA RECORD CONTENTS

Record Type—950
User's Name—952
Current Status of Food Collection Process—954
Weigh-in Code—956
Weigh-out Code—958
Plate Weigh code—960
Weights—962
Dates—964
Times—966
Start Video Frames—968
Stop Video Frames—970
Text Fields—972
Computer Code—974
Serial Number of Computer Data Collected On—976

A single data record is created for each food weighed-in. The data record is continually referred to for information by the control and logic system 2 (FIG. 1), and is also continually updated until all weighing information has been received, a food code assigned, and any adjustments to the data record recorded. In addition to the basic food intake record, there are several other record types including merged leftovers, comments, forgotten items, and spills data records. These data records utilize the fields of the basic food intake record: however, they use the fields in different ways.

Within a data record, "Record Type" 950 is denoted by a double digit number representing the record type, such as "07" indicates that this record is a "comments record". "User's Name" 952 identifies which individual the record belongs to. "Current Status of Food Collection Process" 954 is a set of code numbers which reference the status of the current record, e.g. 1=food has been weighed-in, 2=record complete, 3=container needs to be weighed, etc. The "Weigh-in Code" 956 identifies which of the weigh-in options was used for weighing the food. Likewise, the "Weigh-out Code" 958 is used to identify the weigh-out option used for the food. "Plate Weigh Code" 960 indicates if a container weight is missing. Since each weigh-in option will result in a different number of possible food weights, a total of 5 food weights could be recorded in "Weights" 962. Four of the 5 weights reflect the food weights in the order of recording. The fifth weight is the net weight of the food consumed. "Dates" 964 and "Times" 966 are the date and time recorded for each transaction, such as each weight, each comment, etc. For "Start Video Frames" 968 and "Stop Video Frames" 970, one video frame number is assigned to each food weight recorded. "Text Fields" 972 contains the user entered food and container descriptions and the user selected food description from the resident food list 804 (FIG. 5.D.3). "Computer Code" 974 contains either the user selected resident food list computer code or an alpha-numeric barcode. "Serial Number of Computer Data Collected On" 972 is the serial identification number of the computer 17 (FIG. 2).

This invention has been described in an exemplary and preferred embodiment, but is not limited thereto. Those skilled in the art will recognize that a number of additional modifications and improvements can be made to the invention without departure from the essential spirit and scope. It is therefore not intended that the invention be limited, except as indicated by the claims.

What is claimed is:

1. An interactive dietary measurement system for measurement of dietary intake of individuals, comprising:

food weight input means for entering food weight data, means for generating food-associated code data, means for processing said food weight data, means for providing user services including provisions of a plurality of options and directives for correct measurements of different foods without need of changing a user's dietary habits, user interactive means coupled to said processing means for permitting the user to communicate with the system, storage means for storing said food weight data, said food-associated code data and processed data, output means for advising the user of various information including said food weight data, said options and said directives, and prompting the user to take next measurement actions.

2. An interactive dietary measurement system of claim 1, wherein said food weight input means includes at least one electronic balance, and said food weight data includes weigh-in data and weigh-out data.

3. An interactive dietary measurement system of claim 1, wherein said means for generating food-associated code data includes a food code administration means for providing a proper food code for each food identified by a user, said administration means including at least one food-list database coupled to said computer means, said food-list being associated with food codes so that a user can enter a food description by said interactive means to match a food description in said database.

4. An interactive dietary measurement system of claim 3, wherein said food-list database includes food group descriptions and food species descriptions under each food group description.

5. An interactive dietary measurement system of claim 1 wherein said food coding means includes a food identification catalogue having a food list with associated barcodes thereon, and a barcode reader coupled to said processing means for reading barcodes into said processing means.

6. An interactive dietary measurement system of claim 1, wherein said user interactive means includes at least one of a keyboard, a mouse, and a voice recognition system.

7. An interactive dietary measurement system of claim 1 wherein said output means includes at least one of a video display means and audio generation means for advising a user of various information and prompting a user to take next measurement actions.

8. An interactive dietary measurement system of claim 1 or 2 wherein said options include a plurality of measurement options for entering food weigh-in data and a plurality of options for entering food weigh-out data, and at least one option for entering food-associated codes.

9. An interactive dietary measurement system of claim 8, wherein said plurality of options for entering food weigh-in data includes a weigh-food option with sub-options for providing respective methods and associated directives for measurements of an empty plate or container, food with a plate or container, and food only; a weigh-drink option with sub-options for providing respective methods and associated directives for measurements of a drink with bottle, can or carton, and drink with a cup or glass; and second-helping option for providing methods and associated directives for measurements of second-helpings of the foods advised of by said output means.

10. An interactive dietary measurement system of claim 8, wherein said plurality of options for entering food weigh-out data include a food and drink weigh-out option with sub-options for providing respective methods and associated directives for measurements of a single food leftover and merged food leftovers; a spill weigh-out option for providing a method and associated directives for entering spilled food data into the system; and an option for providing a method and associated directives for allowing a user to enter data related to forgotten items.

11. An interactive dietary measurement system of claim 8 wherein said option for entering food-associated codes includes utilization of barcodes and a food-list data-base for generating the food-associated codes.

12. An interactive dietary measurement system of claim 1 wherein said user services further include questions and comments entering option for providing methods and associated directives for entering questions or comments into the system.

13. An interactive dietary measurement system of claim 1 wherein said user services also include an immediate advisement service for advising a user of weighing errors through said output means and for allowing a user to correct errors stored in said storage means.

14. An interactive dietary measurement system of claim 9 wherein said plurality of food weigh-in options further includes a recipe food weigh-in option for providing methods and associated directives for entering weight data of recipe food.

15. An interactive dietary measurement system of claim 1 further including a system clock means for providing time data for each recorded food weight data.

16. An interactive dietary measurement system of claim 1 further including video camera and recorder means for recording and storing video image data for later digital transmission to said storage means of the system.

17. An interactive dietary measurement system of claim 1 further including at least one food nutrient or components database means for providing nutrient or component data for each said food code which is transferred from said storage means and associated with a food eaten by the user, and a calculation and analysis means for calculating and analyzing food nutrients or components for the food eaten by the user.

18. An interactive dietary measurement system of claim 17, wherein said calculation and analysis means is incorporated in said processing means.

19. An interactive dietary measurement system of claim 1 further including a modem means for coupling the system with a telephone line so that the system can communicate with separate food component databases and analysis systems.

20. An interactive dietary measurement system for measurement of dietary intake of users, comprising:
    weight input means for entering weigh-in and weigh-out data,
    display means for display of various information,
    data collection means for collecting food intake data, said data collection means including:
    user interactive means for permitting a user to communicate with the system,
    database means for providing a food code for each recorded food response to food descriptions entered from said interactive means,
    storage means for storing recorded weight data and associated food code data,
    means for controlling operation and processing of entered data, said means for processing of entered data further providing a plurality of measurement options with respective directives for different food services through said display means, said weigh-in data being tagged according to food services in said storage means in order to track the measurements of each said option in use and to advise the user of the current entered data and the next action in the measurement.

21. An interactive dietary measurement system of claim 20 wherein said means for processing of entered data also advises a user of weighing errors through said display means and allows a user to correct said weighing errors stored in said storage means.

22. An interactive dietary measurement system of claim 20 wherein said weigh-in and weigh-out data includes food weight input data and food container weight input data.

23. An interactive dietary measurement system of claim 20 wherein said display means includes video display means and audio display means.

24. An interactive dietary measurement system of claim 20 further including a food identification catalogue having a food list with associated barcodes thereon, and at least one barcode reader coupled to said processing means for reading barcodes into said storage means.

25. An interactive dietary measurement system of claim 20 wherein said measurement options include a plurality of weigh-in and weigh-out options for providing respective methods and associated directives for entering weigh-in and weigh-out data for said different food service situations.

26. An interactive dietary measurement system of claim 20 or 25 wherein said different food services include at least a food-only service; a food with container service; a drink with container, bottle, carton or cup service; a pre-packaged food service; a drink with food or ice service; and a recipe food service.

27. An interactive dietary measurement system of claim 25, wherein said weigh-in options also include a second helping option for entering said weigh-in data of a second helping of foods listed on said display means.

28. An interactive dietary measurement system of claim 20 wherein said processing means further allows a user to enter notes or comments into said storage means.

29. An interactive dietary measurement system of claim 20 further including a food analysis means for providing a report on analyzed intake of nutrients or components, said analysis means including a nutrients or component database means for providing data of nutrients or components associated with eaten foods, and a processing means for processing said collected food intake data in combination with said nutrient or component database means to produce said report.

30. An interactive dietary measurement system of claim 20 further including a modem means for coupling said data collection means with a telephone line in order to allow communication with said food analysis means.

31. An interactive dietary measurement system of claim 20, wherein said processing means also includes a clock means for providing time data to each of said weigh-in and weigh-out data.

32. An interactive dietary measurement system of claim 20, wherein said database means includes food lists and associated food codes, each food name in each of said food lists including a food description so that a user can easily find words to match the food description in said food list.

33. A method for measurement of dietary intake by using a computer or microprocessor which includes a storage means for storing recorded data and processed data, said method comprising the steps of:
    entering weigh-in and weigh-out data into said computer through an electronic balance connected to said computer, displaying a variety of information on a display connected to said computer, storing and displaying a plurality of weigh-in options for different food services or habits for allowing a user to make a weigh-in measurement selection, advising a user of said weigh-in measurement in advance, through said display, for each of said weigh-in options selected by users through an input device, tagging said weigh-in data with respect to said different weigh-in options in use, storing and displaying a plurality of weigh-out options for different food leftover services or habits for allowing users to make a weigh-out measurement selection, advising users of measurement actions in advance through said display means for each of said weigh-out options selected by users through said input device.

34. A method of claim 33 further including a step of tracking the measurement record so as to advise a user of the current measurement record through said display means.

35. A method of claim 33 further including a step of checking weight data changes under predetermined criteria to advise a user of any measurement errors and allow a user to make corrections.

36. A method of claim 33 wherein said step of storing and displaying a plurality weigh-in options further includes a step of providing a weigh-food option with sub-options for providing methods and associated directives for measurements of an empty plate or container, food with a plate or container, and food only; a weigh-drink option with sub-options for providing respective methods and associated directives for measurements of a drink with bottle, can or carton, and drink with a cup or glass; and a second-helping option for providing methods and associated directives for measurements of second-helpings of the foods advised of by an output device.

37. A method of claim 33, wherein said step of storing and displaying a plurality of weigh-out options further includes a step of providing a food and drink weigh-out option with sub-options for providing respective methods and associated directives for measurements of a single food leftover and merged food leftovers; a spill weigh-out option for providing a method and associated directives for entering spilled food data into the system; and an option for providing a method and associated directives for allowing users to enter data related to forgotten items.

38. A method of claim 33 further including a step of processing said weigh-in and weigh-out data for providing a complete food intake data record.

39. A method of claim 33 further including steps of coupling a food code administration database with said computer and allowing user interactions with said computer to search an appropriate food code for each recorded food.

40. A method of claim 33 further including a step of generating and storing time data associated with food measurement data stored in said storage means.

41. An interactive measurement apparatus for accurate measurement of dietary intake of users without need of assistance from dietary staff or changing a user's dietary habits, comprising:

data input means for entering food weigh-in and weigh-out data, said data input means including weight input means and alphanumeric input means;

calculation and control means for producing correct dietary intake data by use of said weigh-in and weigh-out data and controlling operation of the apparatus;

food identification means for storing a plurality of food group names and food names including a plurality of combination food names, each of said food names being associated with a code or codes representing descriptions of said combination foods;

means for providing user services including provisions of a plurality of options and directives for correct measurement of different foods without need of changing a user's dietary habits;

means for generating feedback signals of errors;

means for informing users of various information including said data entered by the users, said user measurement options and directives, said feedback signals and processed results.

42. The apparatus of claim 41 wherein said food identification means includes at least a computer database.

43. The apparatus of claim 41 wherein said means for informing users of various information includes at least a video display means and an audio generation means.

44. An interactive dietary measurement apparatus of claim 41 or 42 wherein said options include a plurality of measurement options for entering food weigh-in data and a plurality of options for entering food weigh-out data, and at least one option for entering food-associated codes.

45. An interactive dietary measurement apparatus of claim 44, wherein said plurality of options for entering food weigh-in data includes a weigh-food option and sub-options for providing respective methods and associated directives for measurements of an empty plate or container, food with a plate or container, and food only; a weigh-drink option with sub-options for providing respective methods and associated directives and measurements of a drink with bottle, can or carton, and drink with a cup or glass; and second-helping option for providing methods and associated directives for measurements of second-helpings of the foods advised of by said output means.

46. An interactive dietary measurement apparatus of claim 44, wherein said plurality of options for entering food weigh-out data include a food and drink weigh-out option with sub-options for providing respective methods and associated directives for measurements of a single food leftover and merged food leftovers; a spill weigh-out option for providing a method and associated directives for entering spilled food data; and an option for providing a method and associated directives for allowing a user to enter data related to forgotten items.

* * * * *